United States Patent
Seder

(10) Patent No.: US 8,061,302 B2
(45) Date of Patent: Nov. 22, 2011

(54) ECHOCARDIOGRAPHIC MEASUREMENTS AS PREDICTORS OF RACING SUCCESS

(75) Inventor: Jeffrey A. Seder, Coatesville, PA (US)

(73) Assignee: Equine Biomechanics and Exercise Physiology, Inc., West Grove, PA (US)

( * ) Notice: Subject to any disclaimer, the term of this patent is extended or adjusted under 35 U.S.C. 154(b) by 0 days.

(21) Appl. No.: 12/414,962

(22) Filed: Mar. 31, 2009

(65) Prior Publication Data

US 2009/0192975 A1    Jul. 30, 2009

Related U.S. Application Data

(63) Continuation of application No. 10/521,087, filed as application No. PCT/US03/19537 on Jun. 20, 2003, now abandoned.

(60) Provisional application No. 60/396,592, filed on Jul. 17, 2002.

(51) Int. Cl.
*A01K 29/00* (2006.01)

(52) U.S. Cl. .......................................... 119/174

(58) Field of Classification Search .................. 119/174
See application file for complete search history.

(56) References Cited

U.S. PATENT DOCUMENTS

| | | | |
|---|---|---|---|
| 4,008,713 A | 2/1977 | Griffith et al. | |
| 4,357,944 A | 11/1982 | Mauser et al. | |
| 4,361,154 A | 11/1982 | Pratt, Jr. | |
| 4,421,119 A | 12/1983 | Pratt, Jr. | |
| 5,100,127 A | 3/1992 | Melnick et al. | |
| 5,680,862 A | 10/1997 | Song et al. | |
| 5,737,280 A * | 4/1998 | Kokubo | 368/2 |
| 5,779,631 A | 7/1998 | Chance | |
| 6,134,460 A | 10/2000 | Chance | |
| 6,358,208 B1 | 3/2002 | Lang et al. | |
| 6,577,897 B1 | 6/2003 | Shurubura et al. | |
| 6,602,209 B2 | 8/2003 | Lambert et al. | |
| 7,269,516 B2 * | 9/2007 | Brunner et al. | 702/19 |
| 2002/0123699 A1 | 9/2002 | Lambert et al. | |
| 2003/0212348 A1 | 11/2003 | Lambert | |

FOREIGN PATENT DOCUMENTS

| | | |
|---|---|---|
| EP | 00302430 | 6/1981 |
| EP | 0083847 A2 | 7/1983 |
| EP | 0083848 A1 | 7/1983 |
| GB | 2400907 | 10/2004 |
| WO | WO 02/13938 A2 | 2/2002 |

OTHER PUBLICATIONS

Bakos, Z. et al., "Two-Dimensional and M-Mode Echocardiographic Measurements of Cardiac Dimensions in Healthy Standardbred Trotters", *Acta Veterinaria Hungarica*, 2002, 50(3), 273-282.

Feigenbaum, H., *Echocardiography*, 1986, 4th ed. Lea & Feiber, Philadelphia, 398-402.

(Continued)

*Primary Examiner* — David Parsley
(74) *Attorney, Agent, or Firm* — Woodcock Washburn LLP

(57) ABSTRACT

The present invention is directed to methods for selecting racehorse candidates. Provided herein are methods for increasing the likelihood of selecting candidates that will be high earners, while reducing the likelihood of selecting candidates that will be low earners, on the basis of certain ultrasonographically-obtained cardiac measurements.

6 Claims, 10 Drawing Sheets

OTHER PUBLICATIONS

Henry, W.L. et al., "Report of the American Society of Echocardiography Committee on Nomenclature and Standards in Two-Dimensional Echocardiography", *Circulation*, 1980, 62(2), 212-217.

Marr, C.M. et al., "Pre-and Post Exercise Echocardiography in Horses performing Treadmill Exercise in Cool and Hot/Humid Conditions", *Equine Exercise Physiology* Suppl 30, 1999, 131-136.

Michael R. O'Grady, et al., "Quantitative Cross-Sectional Echocardiography in the Normal Dog", *Veterinary Radiology*, 1986, 27, 34-49.

Pascoe, J.R. et al., "Cardiac Output Measurements using Sonomicrometer Crystals on the Left Ventricle at Rest and Exercise", *Equine Exercise Physiology*, 1999, 30, 148-152.

Seder, J.A. et al., "Double and Triple Fully Airborne Phases in the Gaits of Racing Speed Thoroughbreds", *Proceedings from the Twelfth Meeting of the Association for Equine Sports Medicine*, Mar. 13-16, 1993, Fallbrook, California, 65-75.

Seder, J.A. et al., "The Relationship of Selected Two-dimensional Echocardiographic Measurements to the Racing Performance of 5431 Yearlings and 2003 Two-year-old Thoroughbred Racehorses," *J. Esqine Veterinary Science*, 2003, 23(5), S5-S72.

Seder, J.A. et al., "Temporal and Kinematic Gait Variables of Thoroughbred Racehorses At or Near Racing Speeds," *J. Esqine Veterinary Science*, 2003, 23 (5), S82-S112.

Slater, J.D. et al., "Echocardiographic Measurements of Cardiac Dimensions in Normal Phones and Horses", *Equine Vet J.*, 1995, 19, 28-32.

*Thoroughbred Times*, Jul. 22, 2000, 51.

Voros, K. et al., "Anatomical Validation of Two-dimensional Echocardiography in the Horse", *Equine Vet, J.*, 1990, Part 1 and 2, 392-402.

Young, L.E. et al., "Measurement of Cardiac Function by Transthoracic Echocardiography: Day to Day Variablity and Repeatability in Normal Thoroughbred Horses", *Equine Veterinary Journal.*, 1998, 30(2), 117-122.

Young, L.E., "Cardiac Responses to Training in 2-Year-Old Thoroughbreds: An Echocardiographic Study", *Equine Exercise Physiology*, 1999, 30, 195-198.

Young, L.E. et al., "Heart Size Estimated by Echocardiography Correlates with Maximal Oxygen Uptake", *Equine Vet J. Suppl.*, 2002, 34, 467-471.

Young, L.E., "Physiological Society Symposium—The Athlete's Heart, Equine Athletes, the Equine Athlete's Heart and Racing Success", *Experimental Physiology*, 2003, 88.5, 659-663.

Young, L.E., "Relative Wall Thickness: A Useful Indicator of Sports-Specific Cardiac Adaptations to Training in Horses", *Journal of Equine Veterinary Science*, 1999, 1999(9), 544-555.

Weyman, A.E., "Normal Cross-Sectional Echocardiographic Measurements in Adults", *Cross-Sectional Echocardiography*, 1982, Appendix B, 497-504.

Wyatt, H.L. et al., "Cross-Sectional Echocardiography I. Analysis of Mathematic Models for Quantifying Mass of the Left Ventricle in Dogs", *Circulation*, 1979, 60(5), 1104-1113.

Declaration Under 37 C.F.R. §1.56 of Jeffrey A. Seder, filed on Mar. 13, 2006 in U.S. Appl. No. 10/521,087, filed Jan. 13, 2005.

* cited by examiner

ECHOCARDIOGRAPHIC MEASUREMENTS AS PREDICTORS OF RACING SUCCESS

CROSS REFERENCE TO RELATED PATENT APPLICATIONS

This application is a continuation of application Ser. No. 10/521,087, filed on Jan. 13, 2005, which is a United States national stage entry of International Application No. PCT/US2003/019537, filed Jun. 20, 2003, which in-turn claims the priority benefit of U.S. Provisional Application No. 60/396,592, filed Jul. 17, 2002. The disclosure of each of these prior applications is incorporated herein by reference in its entirety for all purposes.

FIELD OF THE INVENTION

The present invention is directed to methods for screening candidate racehorses, and improving the likelihood of selecting a candidate that will become a successful racehorse.

BACKGROUND

For centuries, perhaps ever since the horse was first domesticated, people have raced their horses against each other, to see which man owned the faster animal. Countless generations of breeding the fastest stallion to the best mares has led to the modern racehorse, a magnificent running machine, genetically selected to excel in the modern version of "the sport of kings," a sport that still thrives across the globe today.

Since the sport first began, people have bought, sold and traded young horses, with dreams of acquiring a horse that might one day mature into a stakes winner. A huge business has developed around the breeding, preparation, and sale of potential racehorses. Potential buyers pore over sales catalogs, searching the horse's parentage and pedigree in hope of selecting a horse that contains just the right mix of speed, stamina, durability and temperament to grow into a successful racehorse. The racing candidate is carefully examined to make sure its legs are straight, the airway is clear, and that there are no physical blemishes or infirmities that might diminish its chance of future success. "Experts," sometimes boasting of years of experience at spotting future champions long before the horse ever sets foot on a racetrack, are regularly consulted to scrutinize the field of candidates, and help the would-be owner select a horse that possess the right conformation, the right carriage, the right glint in the eye—the stuff of champions.

But despite all the statistical analysis of pedigree, the pre-sale poking and prodding, and the intense scrutiny of a countless number of trained eyes, separating the future winners from the future losers has remained an inexact science at best. In a study of all named (i.e., registered) Thoroughbred foals born between 1985 and 1994, only about 30% ever started a single race, and the average earnings per start of all foals was only $1,378. Selecting the offspring of the top 1% of stallions reduced the percentage of non-starters to about 15%, and increased the average earnings per start to over $3,000, but still, a large percentage of all young horses sold at auction fail to recoup their original purchase price. One has only to look to the results of this year's Kentucky Derby to see how inaccurate the selection of racehorse candidates can be: the race was won by Funny Cide, once a $75,000 purchase, while numerous horses from the same crop that sold for much more, even ten or more times as much, failed to even win a single maiden race.

Accordingly, better methods for screening potential racehorse candidates are needed, particularly methods that will increase the chances of selecting a horse that is more likely to become a high earner, while decreasing the likelihood of selecting a horses that will turn out to be a low earner. The present invention is directed to these, as well as other ends.

SUMMARY OF THE INVENTION

It has now been discovered that certain objective measurements that may be readily obtained from young horse racing candidates, e.g., heart and/or spleen size, may be used as predictors of the future racing success. Accordingly, the present invention provides methods of screening a racehorse candidate and selecting a racehorse candidate likely to become a high-earner racehorse.

The method for screening racehorse candidates includes the step of obtaining one or more measurements, including echocardiographic measurements, from a racehorse candidate and comparing the measurements to a collection of corresponding measurements from a group of horses. In particular, in one embodiment, the methods include the step of obtaining a measurement of the width of the ventricular septal wall of a racehorse candidate and comparing it to ventricular septal wall width measurements from a group of horses of similar age, sex, and weight. In another embodiment, the methods of the present invention further comprise the steps of obtaining one or more measurements selected from the cross-sectional area of the left ventricle in diastole, the cross-sectional area of the left ventricle in systole, the body size (more specifically, the height X weight), or the splenic cross-sectional area of the candidate racehorse and comparing these additional measurements to corresponding measurements from the group of horses.

In another embodiment of the present invention, the methods of the present invention include the step of obtaining a measurement of the splenic cross-sectional area of a racehorse candidate and comparing it to splenic cross-sectional area measurements from the group of horses. In another embodiment, the methods of the present invention further comprise the steps of obtaining one or more measurements selected from the cross-sectional area of the left ventricle in diastole, the cross-sectional area of the left ventricle in systole, the body size, or the interventricular septal wall width of the candidate racehorse and comparing these additional measurements to corresponding measurements from the group of horses.

After the measurements have been obtained from the candidate racehorse, the methods of the present invention may further include the step of selecting a racehorse candidate if its ventricular septal wall width measurement is greater than the mean ventricular septal wall width of the group of horses. In another embodiment, the methods of the present invention may further include the step of selecting a racehorse candidate if one or more of its measurements, e.g., ventricular septal wall width, left ventricle cross sectional area in diastole or systole, body size, splenic cross sectional area, is greater than the mean corresponding measurement from the group of horses of similar age, weight and sex.

In yet another embodiment, the methods of the present invention may further include the step of selecting a racehorse candidate if one or more of its measurements, e.g., ventricular septal wall width, left ventricle cross sectional area in diastole or systole, body size, splenic cross sectional area, is in the $75^{th}$ percentile or higher when compared to corresponding measurements from the group of horses. The methods of the present invention may also include the step of rejecting a racehorse candidate if one or more of its measurements, e.g., ventricular septal wall width, left ventricle cross sectional area in diastole or systole, body size, splenic cross sectional area, is not in the 75th percentile or higher when compared to corresponding measurements from the group of horses.

In one aspect of the present invention, the measurements obtained from the horses are acquired using standard methods, commonly known and accepted in the art. In another aspect, the ventricular septal wall width measurement is obtained by measuring a particular structure in an echocardiographic image of the heart, the measurement running from the attachment of the moderator band through the interventricular septum into the right ventricle to the endocardial edge of the right ventricular free wall where the wall attaches to the interventricular septum. In yet another embodiment, the left ventricle in diastole and/or systole cross sectional area is obtained by measuring the circumference of the left ventricular chamber.

The methods of the present invention thus improve the odds of selecting high and excluding low earner racehorses. Additionally, from within the group of high earners, certain parameters may be applied that enable the selection of horses more likely to be high earners in races that extend beyond a mile. These and other applications for the methods disclosed herein will be made apparent in the detailed description and examples that follow.

DETAILED DESCRIPTION OF THE INVENTION

Figure 1:
FIG. 1: A left parasternal short-axis echocardiogram of the left ventricle at peak systole from a 2-year-old Thoroughbred filly with a resting heart rate below 40 bpm obtained from the left cardiac window with a 3.5 MHz probe. The dotted line traces the endocardial border of the left ventricle at peak systole.

The present invention provides new methods for screening a racehorse candidate. The present invention relates, in part, to the discovery that certain physical characteristics of the racehorse candidate that can be readily measured may be used as a predictor of the horse's future racing ability.

In particular, it has been found that certain echocardiographic features are correlated with racing success, and may be used to screen racehorse candidates. Accordingly, the present invention provides, inter alia, methods of obtaining certain physical measurements of a candidate racehorse's heart.

The present invention also relates, in part, to the discovery that the size of a horse's spleen can also be used as a predictor of the horse's future racing ability. Accordingly, the present invention provides methods of screening a racehorse candidate on the basis of its splenic cross-sectional area.

It has also been found that a horse's physical size for it's chronological age, particularly when viewed in combination with certain cardiac parameters or splenic cross sectional area, can be used to predict the racing ability of a candidate racehorse. Accordingly, the present invention provides screening methods that further include the step of determining the physical size of a horse. For the purposes of the present invention, the physical size or body size of a horse or "HTWT" is determined by multiplying the height and the weight of the horse. Methods of determining the height and weight of a horse are known in the art, e.g., using a scale, weight tape, height stick, or well-educated estimates based on visual inspection by those skilled in the art.

In the methods of the present invention, the heart of a horse is measured in terms of one or more of the following variables: cross sectional area of the left ventricle in diastole (LVD), cross sectional area of the left ventricle in systole (LVS), ventricular septal wall width, and percent change in ventricular area per stroke (PS).

The term "ventricular septal wall width" refers to the width of the septum dividing the right and left ventricles. A particularly preferred ventricular septal wall measurement involves a particular cardiac structure that runs from the endocardial edge of the right ventricular free wall, at the point where the wall meets the interventricular septum, through the interventricular septum, to the point of attachment of the moderator band in the left ventricle, as shown for example in FIG. 3. This structure may be readily identified in a left parasternal short-axis view, preferably obtained at end diastole, although other views may also be used to obtain measurements of this structure. Measurements of this particular structure are referred to herein as the "interventricular septal wall structural thickness" or "SW".

The "cross-sectional area of the left ventricle in systole" or "LVS" is measured when the left ventricle contracts to its smallest size in systole. The "cross-sectional area of the left ventricle in diastole" or "LVD" is measured when the left ventricle expands to its largest size in diastole. These measurements can be obtained by any means known to those of ordinary skill in the art, for example, by using the "inner edge" method. In the "inner edge" method, linear parameters are measured from the inner edge of endocardial surfaces and areas are traced along the inner borders of the endocardial echoes. Thus, LVS and LVD may be determined by freezing, for example, a left parasternal short-axis two dimensional echocardiographic ultrasound image at the peak of systole, and the end of diastole, respectively, and tracing the internal perimeter of the left ventricular chamber using calipers on the ultrasound machine. The area inside the tracing is then calculated based on a pixel count (512×512 for total screen). Many commercially available diagnostic ultrasound machines include software capable of measuring a circumscribed area in this fashion.

Alternatively, the cardiac measurements cited herein may be measured by any method known to those of skill in the art, as may be described, for example, in one or more of the following: Voros et al., (1990) *Equine Vet. J.* p. 392-397; Weyman, A. E. (1982) Cross-sectional echocardiography, Lea & Febiger, Philadelphia, p. 497-504; Wyatt, et al. (1979) *Circulation* 60, p. 1104-1113; O'Grady et al. (1986) *Vet. Radiol.* 27, p. 34-49; Henry, W. L., et al. (1980) *Circulation* 62, p. 212-217; Feigenbaum, H. (1986) Echocardiography, 4th edn. Lea & Febiger, Philadelphia; Voros, et al, *Equine vet. J.* p. 398-402; Young, L. E., and Scott, G. R. (1998) *Equine vet. J.* 30 (2) p. 117-122; Slater, J. D. and Herrtage, M. E. (1995), *Equine vet. J.*, Suppl. 19, p. 28-32; Marr, et al., *Equine vet. J.*, Suppl. 30, p. 131-136; Young et al., (1998), *Equine vet. J.* 30 (2) p. 117-122; Young, L. E. (1999) *Equine vet. J., Suppl.* 30, p. 195-198; Pascoe, J. R., et al., (1990) *Equine vet. J., Suppl.* 30, p. 148-152.

The "percent change in ventricular area per stroke" or "PS" is computed by subtracting LVS from LVD, dividing the resultant number by LVD and multiplying by 100, e.g., $$PS = \frac{LVD - LVS}{LVD} \times 100.$$

Thus, PS may be correlated with the volume of blood that is ejected from the heart per stroke, at rest.

In the methods of the present invention, the splenic cross sectional area or "SPLN" is obtained by producing a cross sectional image of the horse's spleen, and determining the cross sectional area of same, as discussed above with regard to the LVD and LVS measurements.

In one embodiment of the present invention, LVS, LVD, and SW are measured from a left parasternal short axis echocardiogram of the left ventricle of the horse at end systole and end diastole. The echocardiogram can be obtained from the left cardiac window using a 3.5 MHz probe. During the electrocardiographic exam, the ultrasound transducer can be held in the right hand with the cursor facing caudally. The left forelimb can be advanced slightly and the transducer can be placed in the 4th or 5th left intercostal space, at a level just dorsal to the point of the olecranon. The transducer beam can be directed perpendicular (horizontal) to the longitudinal cardiac axis. The resulting image provides a nearly circular appearance to the left ventricular lumen. Moving (angling) the transducer beam from the apex to the base of the heart, the moderator band(s), papillary muscle, chordae tendinae and septal leaf of the mitral valve can be identified and used as intracardiac reference points to obtain reproducible cardiac images in the same tomographic plane. In other embodiments of the present invention, alternate echocardiogram views may be obtained and the cardiac and splenic size measured from the alternate views, e.g., right parasternal short axis view, left or right parasternal long axis view, apical views. Typically three to five cardiac cycles are measured for each echocardiographic measurement. This helps minimize error, for example, in the timing of peak systole, and end diastole. Short axis images can be projected according to international terminology based on the recommendations of the American Society of Echocardiography (Henry 1980, supra; Feigenbaum 1986, supra). Short axis images recorded from the left side of the chest can be projected as though the tomographic planes are viewed from the base to the apex of the heart.

The accuracy of the measurements may be compromised when a horse's heart is beating very quickly. For example, in a very rapidly beating heart, it may be difficult to accurately freeze the image at peak systole, or at end diastole. Accordingly, it is preferred that the measurements be taken when the horse's resting heart rate is less than about 50 beats per minute, with a resting heart rate at the time of examination of less than about 40 beats per minute being even more preferred.

The present invention also provides a collection of measurements from a group of horses for comparison with those obtained from the candidate racehorse. In order to create a collection or database of horse measurements, selected measurements are obtained from a group of horses, as discussed above. The database preferably includes measurements of each of the variables LVD, LVS, PS, HTWT, SPLN, and ventricular septal wall width, particularly the variable SW, as defined above. Of course, obtaining measurements from a large number of individuals will minimize statistical aberrations, and therefore improve the predictive accuracy of the methods disclosed herein. Typically, the group of horses includes at least about 1000 individuals, with a group of greater than 5000 horses being preferred. Even more preferably, the database will include measurements of at least about 7500 individuals.

Since most racehorse candidates are sold as yearlings or two-year olds, it is preferred that the individuals making up the group of horses range in age from about 12 months to about 28 months of age chronologically. It has been found, however, that cardiac measurements vary, depending on age, sex, and weight, making it difficult to compare horses on the basis of cardiac measurements alone, without adjusting for the effects of these parameters. Accordingly, an adequate comparative sample of horses of about the same age, sex and weight as the racehorse candidate is preferred. Preferably, the group of horses used for the comparison are of the same breed as the racehorse candidate, and that breed is preferably Thoroughbred. As used herein, the term "about the same age, sex and weight" means that the individuals making up the collection of horses used for comparative purposes have a date of birth within about 30 days of the racing candidate, are of the same genetic gender, and have a weight of within about 25 pounds of the racing candidate. Preferably, the database will include cardiac measurements of at least about 35 horses of the same age, sex and weight as the racehorse candidate. More preferably, the cardiac measurements of the candidate racehorse are compared to a database that includes cardiac measurements of at least about 75, and even more preferably at least about 150, and still more preferably, at least about 300 horses of the same age, sex and weight as the racehorse candidate. As a result of such a large statistical sample, greater accuracy and predictive ability may be achieved by the methods described herein.

Once a database of sufficient size has been generated to assure a statistically significant number of horses of about the same age, sex and weight as the racehorse candidate have been obtained, a comparison can be readily made. For example, the candidate and each horse in the group may be ranked according to each measurement on a scale from 0 to 100. Percentiles for each measurement may then be calculated using the following equation:

$$\frac{R - 0.5}{N},$$

wherein R equals rank and N equals the number of horses. For example, if there are 100 colts of similar age and weight, and one colt has the $93^{rd}$ largest LVD, he would have an LVD percentile of 92.5%.

$$\frac{93.0 - 0.5}{100} = 92.5\%$$

By reporting the measurements in terms of percentiles, determined relative to other horses of the same sex, age (within 30 days) and weight (within 25 pounds), the cardiac measurements become independent of a horse's age, sex and weight. Thus, the racehorse candidate may be assigned a percentile rank for each measurement variable, e.g., LVD, LVS, SW, SPLN, HTWT, and/or PS, as compared to a statistically significant sample of horses of about the same age, sex and weight.

Other methods for assigning a relative rank to the racing candidate are known to those of skill in the art, and may be used as an alternative to the percentile system described above. For example, standardized scores may be obtained, wherein the standardized score for each horse in the group is determined by subtracting the mean measurement for the group from the observed measurement of an individual horse, and dividing the result by the standard deviation for that variable for the group. Such alternative methods should be considered to merely be variants of the percentile method described above, and do not represent alternative embodiments of the instant invention.

This comparison can be used to predict the racing ability of the candidate racehorse, e.g., whether the candidate racehorse will be more likely to become a high earner or lower earner. For example, as described more fully in the examples to follow, by selecting a racehorse candidate having a ventricular septal wall width greater than the mean ventricular septal wall width of a group of horses of about the same age, sex and weight, and/or rejecting a racehorse candidate that has a septal wall width less than the mean, the likelihood of selecting a high earner racehorse is significantly improved. The odds of selecting a high earner racehorse are further improved by selecting a racehorse candidate that has a ventricular septal wall width that is in the $75^{th}$ percentile or higher, and/or rejecting a candidate that has a septal wall width that is lower than the $75^{th}$ percentile. Conversely, the odds of selecting a low earner are decreased by selecting a horse that has a ventricular septal wall width greater than the mean ventricular septal wall width of a group of horses of about the same age, sex and weight, with the odds of selecting a low earner even further reduced by selecting a racehorse candidate that has a ventricular septal wall width that is in the $75^{th}$ percentile or higher.

Similarly, by selecting racehorse candidates on the basis of measurements for other variables and/or combinations of variables discussed herein, including LVD, LVS, SPLN, HTWT, SW and PS, the likelihood of selecting a candidate that will be a high earner may be increased, and the likelihood of selecting a candidate that will be a low earner will be reduced. Thus, certain embodiments of the present invention are directed to methods that comprise selecting horses that exhibit one or more of the aforementioned measurements greater than the mean measurement, and preferably fall in the $75^{th}$ percentile or higher, than is seen in a group of horses of about the same age, sex and weight.

Additionally, as discussed in more detail in the examples to follow, using the methods of the present invention, in addition to increasing the likelihood of identifying a racehorse candidate that will be a future high earner racehorse, the methods of the present invention can also be used to increase the likelihood of selecting a horse that will be a high earner router, as opposed to a high earner sprinter. As used herein, a "sprint" is a race of 1 mile (8 furlongs) or less, while a "route" race is one of at least about 8.5 furlongs. Since the majority of graded stakes races for Thoroughbred horses in both the United States and Europe (i.e., the races with the highest purses) are contested at distances of greater than 1 mile, it may be advantageous to select a racehorse candidate with an increased likelihood of being a high earner router.

Moreover, after conducting measurements on over 7000 Thoroughbred yearling and two-year old racing candidates, and subsequently following their racing careers (as discussed more fully in the examples to follow) it has been found that extremely high earners, i.e. horses that earned at least $250,000 by the end of their three-year old year, were about three times more likely to have above average HTWT and LVD measurements, when compared to a group of horses of about the same age, sex and weight, than to have below average HTWT and LVD measurements. Accordingly, these variables may be used in the methods of the present invention to increase the likelihood of selecting a racehorse candidate that will be an extremely high earner.

The present invention also provides methods for maintaining a horse registry system or database. Such a system can be managed using bioinformatics. Bioinformatics is the study and application of computer and statistical techniques to the management of biological information. Thus, in one embodiment, the present invention provides a method for populating a database with the biological information obtained using the methods of the present invention. For example, a database can be populated with LVD, LVS, PS, HTWT, SPLN and ventricular septal wall width measurements from a group of horses whose racing abilities are known. Once a database of sufficient size has been generated, the racing ability of racehorse candidates can be predicted as described above, e.g, by comparing measurements from racehorse candidates to corresponding measurements from a group of horses of about the same age, sex, and weight and ranking the horses according to each measurement. Measurements from the racehorse candidates can be optionally entered into the database as well.

In another embodiment, the present invention also provides an apparatus for automating the methods of the present invention, the apparatus comprising a computer and a software system capable of comparing and standardizing echocardiographic and other measurements from horses. The data is inputted in computer-readable form and stored in computer-retrievable format. The present invention also provides computer-readable medium encoded with a data set comprising profiles, e.g., LVD, LVS, PS, HTWT, SPLN, and ventricular septal wall width measurements, of horses known to be high earners, low earners, high earner routers, or high earner sprinters. The information in the data set can be used for comparison purposes in order to improve one's odds of selecting a higher earner racehorse. It can also be used by handicappers or others in order to evaluate horses for betting purposes.

The methods described herein for obtaining certain measurements from horses provides information which can be used to determine the racing ability of candidate racehorses. Although the data generated from the methods of this invention is suited for manual review and analysis, in a preferred embodiment, prior data processing using high-speed computers is utilized.

The invention also provides for the storage and retrieval of a collection of profiles and comparisons in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays.

This invention also preferably provides a magnetic disk, such as an IBM-compatible (DOS, Windows, Windows 95/98/2000, Windows NT, OS/2, etc.) or other format, e.g., Linux, SunOS, Solaris, AIX, SCO, Unix, VMS, MV, Mactinosh etc., floppy diskette or hard (fixed, Winchester) disk drive, comprising a bit pattern encoding data collected from the methods of the present invention in a file format suitable for retrievable and processing in a computerized comparison or relative quantification method.

The invention also provides a network, comprising a plurality of computing devices linked via a data link, such as an Ethernet cable (coax or 10BaseT), telephone line, ISDN line, wireless network, optical fiber, or other suitable signal transmission medium, whereby at least one network device comprises a pattern of magnetic domains and/or charge domains comprising a bit pattern encoding data acquired from the methods of the invention.

The invention also provides a method for transmitting data that includes generating an electronic signal on an electronic communications device, such as a modem, ISDN terminal adapter, DSL, cable modem, ATM switch, or the like, wherein the signal includes (in native or encrypted format) a bit pattern encoding data collected using the methods of the present invention.

In a preferred embodiment, the invention provides a computer system for performing the methods of the present invention. A central processor is preferably initialized to load and execute the computer program for alignment and/or comparison of results. Data is entered into the central processor via an I/O device. Execution of the computer program results in the central processor retrieving the data from the data file.

The target data or record and the computer program can be transferred to secondary memory, which is typically random access memory. For example, a central processor can be a conventional computer; a program can be a commercial or public domain molecular biology software package; a data file can be an optical or magnetic disk, a data server, or a memory device; an I/O device can be a terminal comprising a video display and a keyboard, a modem, an ISDN terminal adapter, an Ethernet port, a punched card reader, a magnetic strip reader, or other suitable I/O device.

The invention also provides the use of a computer system, such as that described above, which comprises: (1) a computer; (2) a stored bit pattern encoding a collection of measurements obtained by the methods of the present invention, which may be stored in the computer; (3) a comparison control; and (4) a program for comparison.

All publications and patent documents cited above are hereby incorporated by reference in their entirety for all purposes to the same extent as if each were so individually denoted.

The below examples are non-limiting and for illustrating the present invention. Alternatives and variations of the below examples within the scope of the present invention as per the below claims may be carried out by a person skilled in the art.

EXAMPLES

Example 1

Selecting the Group of Horses

Selected two dimensional echocardiographic (2DE) measurements were recorded for 5,431 yearling and 2,003 two-year-old Thoroughbred racehorses between the ages of 12 through 28 months. These were unique, unraced horses. Cardiac measurements were recorded primarily at select public yearling and two-year-old auctions between 1995 and 2000. All descriptive statistics used only the most current 2DE measurements from each horse, in order to prevent multiple measurements of the same horse from overly influencing statistics within small groups of horses. Using the most recent measurement of the same horse also maximized the number of two-year-olds available for the study. Among the 7,434 unique horses, there were 2,940 fillies (40%), 4,494 colts (60%), 5,431 yearlings (73%), and 2,003 two-year-olds (27%).

Additionally, 5,909 horses (79%) were at least three years of age by 1 Jan. 2000. Among these horses, by the end of their three-year-old year, 1,156 (20%) raced outside of North America (foreign) and 4,753 (80%) stayed in North American. Among the North American horses, 1,073 (23%) never raced and 3,680 (77%) started at least once (see Table 1).

TABLE 1

Number of Races through Three-Year-Old Year
Among Horses Categorized as North American

| Number of Races through 3-Year-Old Year | Number of Horses | Percent of Total | Cumulative Percentage |
| --- | --- | --- | --- |
| Unraced | 1,073 | 22.58 | 22.58 |
| 1-5 | 1,274 | 26.80 | 49.38 |
| 6-10 | 1,215 | 25.56 | 74.94 |
| 11-15 | 784 | 16.50 | 91.44 |
| 16-20 | 297 | 6.25 | 97.69 |
| 21-25 | 95 | 2.00 | 99.69 |
| 26-30 | 13 | 0.27 | 99.96 |
| 31-35 | 1 | 0.02 | 99.98 |
| 36-40 | 1 | 0.02 | 100.00 |
| Total | 4,753 | 100.00 | 100.00 |

Data from horses with resting heart rates above 40 beats per minute was excluded from this study. The same technician, ultrasound equipment and measurement protocol, as described in the materials and methods section of this paper, was used for all horses studied. Comments regarding physical appearance, body condition, and conformation were recorded during each examination. Table 2, below, provides some perspective to the figures in Table 1.

TABLE 2

Averages for the Breed
Worldwide Performances of Named Thoroughbred Foals
Born in North America between 1985-1994
(Source: *Thoroughbred Times*, Jun. 8, 2002, p. 31)

| Subset of Population | Foals of 1985-1994 | Foals by Top 1% of Sires |
| --- | --- | --- |
| % Starters/foals | 68.9% | 84.8% |
| % Stakes winners/foals | 3.2% | 9.1% |
| % Graded stakes winners/foals | 0.7% | 3.6% |
| % Grade 1 stakes winners/foals | 0.2% | 1.2% |
| % 2-year-old starters/foals | 33.5% | 46.2% |
| % 3-year-old starters/foals | 59.0% | 76.6% |
| % 4-year-old starters/foals | 44.0% | 57.1% |
| % 5-year-old and up starters/foals | 26.5% | 36.9% |
| Average career starts/foal | 14.5 | 18.7 |
| Average career starts/starter | 21.1 | 22.0 |
| Average win distance in furlongs | 6.82 | 7.24 |
| Average earnings/starter | $29,102 | $71,349 |
| Average earnings/start | $1,378 | $3,242 |

Note:
Top 1% of sires determined by total progeny earnings for 1985-1994.

TABLE 3

Sale to Racetrack Performance of 1990-1999 Graduates of Major Yearling Sales
(Source: Thoroughbred Times, Jul. 6, 2002, p. 20)

| SELECT YEARLING AUCTION NAME & LOCATION | No. Horses Sold | Median Sale Price | Avg. Earnings | Starters (%) | Starts Per Starter | Starts Per Foal | Pct. Wnrs. | Pct. Stakes Wnrs. | Pct. Graded Stakes Wnrs. | Avg. Win Dist. |
|---|---|---|---|---|---|---|---|---|---|---|
| Fasig-Tipton Kentucky - July | 1,792 | $35,000 | $61,132 | 1,577 (88.0%) | 19.2 | 16.9 | 68.5% | 6.9% | 2.7% | 6.99 |
| Keeneland Kentucky - July | 1,945 | 235,000 | 112,752 | 1,672 (86.0%) | 14.7 | 12.7 | 62.1% | 11.3% | 6.3% | 7.91 |
| Keeneland Kentucky - September | 28,176 | 22,000 | 48,768 | 24,130 (85.6%) | 20.0 | 17.1 | 64.9% | 6.4% | 2.0% | 7.01 |
| Fasig-Tipton Saratoga - August | 1,535 | 105,000 | 78,696 | 1,338 (87.2%) | 16.8 | 14.7 | 65.8% | 10.0% | 4.5% | 7.53 |

TABLE 4

Averages Among Horses in this Study
Statistics through the Three-Year-Old Year of Study Horses
Horses not Known to have Raced Outside of North America

| Subset of Study Population | All Horses in this Study |
|---|---|
| % Stakes winners | 6.25% |
| % Graded stakes winners | 2.90% |
| % Grade 1 stakes winners | 1.09% |
| % At Least Stakes Placed (including winners) | 12.57% |
| % At Least Graded Stakes Placed (including winners) | 5.14% |
| % At Least Grade I Stales Placed (including winners) | 1.48% |

Note: Includes unraced horses. Race dollar amounts earned can be compared between horses without currency or country distortions. Compare percentages in this table to those of the top 1% of sires' progeny, shown in Table 2.

Performance records. All horses used to predict performance had race records through their three-year-old year. Race records included race date, racetrack, race number, distance raced, level of race, claiming price, finish position and earnings. Horses that raced outside of North America were identified as "foreign," and their race records were not used, since they were often incomplete or difficult to compare with North American records on the basis of dollar value or race level.

Sample Bias. There were pedigree and conformation biases, since the horses examined at "select" public auctions were pre-selected by auction companies based on above-average commercial assessment of pedigree and conformation. Not all horses at each auction were measured, nor were subjects randomly selected. Horses were further pre-selected horses for cardiac measurement based on additional criteria.

Pre-selection biases were reflected in the percentage of stakes winners among horses measured. For example, midway through the 1990 foal crop's ten-year-old year, 2.3 percent had won a stakes race (Thoroughbred Times, Jul. 22, 2000, p. 51). In contrast, 6.7 percent of horses measured for this study, and which were not known to have raced outside of North America, won a stakes race before they were four years old.

Example 2

Measurement Equipment and Techniques

A Pie Medical, digital cineloop scanner 200 from Classic Medical, (Tequesta, Fla.), with a 3.5 MHz annular array, multiring crystal transducer with a 30-cm field of view at 22 frames per second was used for all measurements. The depth of display varied from 15 to 25 centimeters depending on the size of the horse. The ultrasound recorder was equipped with electronic calipers that were used to measure the stored images at the time of the examination.

SAS release 6.12 (SAS Institute, Cary, N.C.), for Windows NT (Microsoft) was used for statistical analysis. Universe (IBM) for Windows 2000 (Microsoft) was used to manage the data. The server was a Dell 2300 Poweredge (Dell, Atlanta, Ga.) with dual 450 MHz Intel Pentium processors, running Windows 2000.

The 2DE imaging protocol was carried out on all horses, by the same, experienced (>5 years) technician to reduce measurement variability. Acoustical coupling gel (Aquasonic 100 ultrasound transmission gel—Parker, Fairfield, N.J.) was applied liberally over the girth area in the 4th and 5th intercostal spaces, starting just below the level of the point of the shoulder down to the level of the olecranon. Three to five cardiac cycles were measured for each variable. Measurements were not made if the heart rate exceeded 40 beats/min., if the heart rhythm was irregular, or if the images were unclear.

During 2DE examination, the ultrasound transducer was held in the right hand with the cursor facing caudally. The left forelimb was advanced slightly and the transducer was placed in the 4th or 5th left intercostal space, at a level just dorsal to the point of the olecranon. From this position, a left parasternal short axis view could be obtained by directing the transducer beam perpendicular (horizontal) to the longitudinal cardiac axis. The image provided a nearly circular appearance to the left ventricular lumen. Moving (angling) the transducer beam from the apex to the base of the heart, the moderator band(s), papillary muscle, chordae tendinae and septal leaf of the mitral valve were identified and then used as intracardiac reference points to obtain reproducible cardiac images in the same tomographic plane.

Except where noted, the short axis images were projected according to international terminology based on the recommendations of the American Society of Echocardiography (Henry 1980, Feigenbaum 1986). Short axis images recorded from the left side of the chest were projected as though the tomographic planes were viewed from the base to the apex of the heart.

The 2DE measurements recorded for all 7,434 horses were measured using electronic calipers. For all dimensions, the "inner edge" method was used (Wyatt et al 1979, Weyman 1982, O'Grady, Bonagura, Powers and Herring 1986), i.e., linear parameters were measured from the inner edge of endocardial surfaces, and areas were traced along the inner borders of the endocardial echoes.

Figure 2:
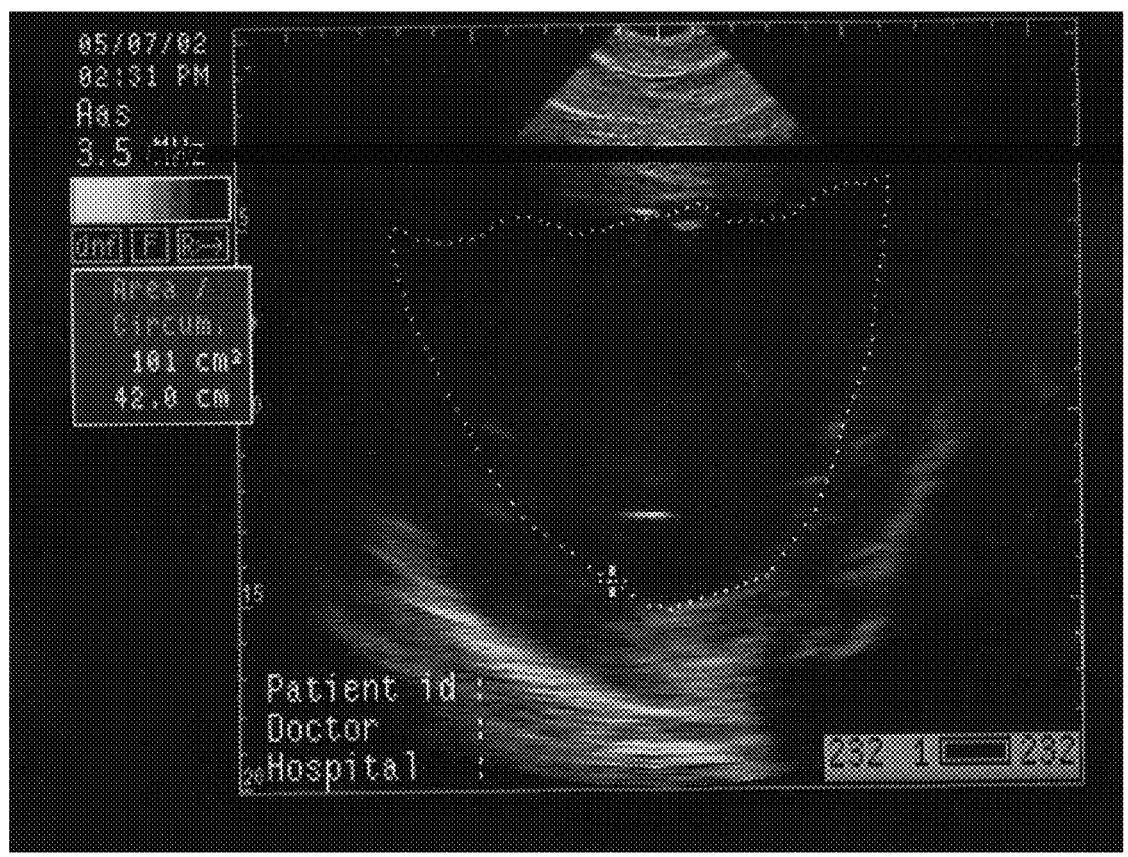
FIG. 2: A left parasternal short-axis echocardiogram of the left ventricle at end diastole from a 2-year-old Thoroughbred filly with a resting heart rate below 40 bpm obtained from the left cardiac window with a 3.5 MHz probe. The dotted line traces the endocardial border of the left ventricle at the end of diastole.
Figure 3:
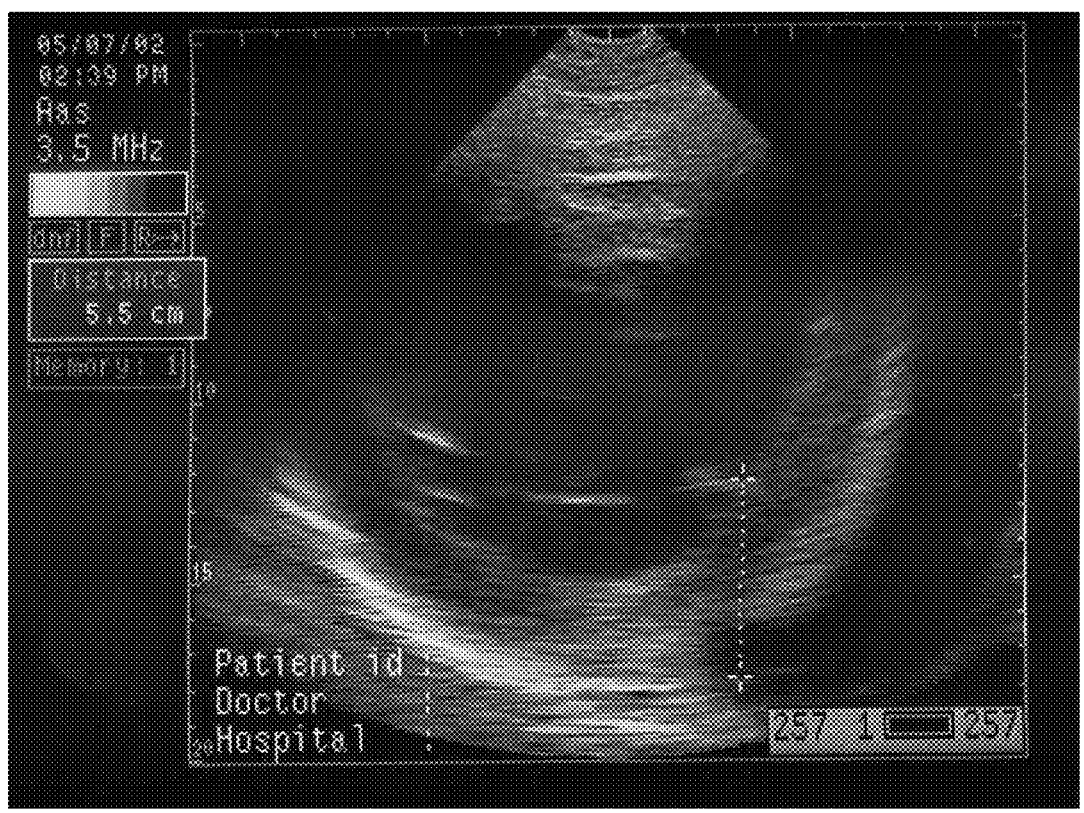
FIG. 3: A left parasternal short-axis echocardiogram of the left ventricle at end diastole from a 2-year-old Thoroughbred filly with a resting heart rate below 40 bpm obtained from the left cardiac window with a 3.5 MHz probe. The dotted line measures the attachment of the moderator band through the interventricular septum into the right ventricular to the endocardial edge of the right ventricular free wall where it attaches to the interventricular septum.

The following variables, as shown and described in FIGS. 1-3, were measured from the stored images: Left ventricular cross sectional area in diastole (LVD); left ventricular cross sectional area in systole (LVS); interventricular septal wall structural thickness in diastole (SW). Percent stroke volume (PS) was computed using the formula:

$$PS = \frac{LVD - LVS}{LVD} \times 100$$

The ultrasound technician estimated HEIGHT and WEIGHT based solely on visual inspection and prior experience. The variable HTWT, which was the product of height times weight, was used in this research as an estimate of overall body size. The ultrasound technician, a life-long horseperson, trained horses prior to this research. While a trainer, she had an on-site horse scale in a 40-stall training facility and took daily weight measurements of horses, and compared scale results to weight tape measurements. Alternatively, a five rating category system was used to describe height and weight. For example, the horses were divided on the basis of weight or height into the following five categories: well below average (at least 1.0 standard deviation below the mean), below average (from 0.5 to 1.0 standard deviations below the mean), average (within 0.5 standard deviations of the mean), above average (from 0.5 to 1.0 standard deviations above the mean), and well above average (at least 1.0 standard deviation above the mean).

Each weight and height measurement was assigned a whole number from 1 to 5, with 1 equal to "well below average" and 5 equal to "well above average." HTPLUSWT was created as the sum of these weight and height ratings, providing an overall physical size estimate. Each horse's cardiac measurements (i.e., LVD, LVS, SW, and PS) were ranked (expressed as a percentile ranging from 0 to 100) relative to those of other horses of the same sex, chronological age, and of the same 1-5 weight group. Stepwise and discriminant results based on the 1-5 weight categories were similar to those results based on estimation of pounds.

Most cardiac measurements varied depending upon age, sex and weight, making it extremely difficult to compare horses on the basis of cardiac measurements without simultaneously adjusting for the effects of these parameters. Two statistical techniques, percentiles and standardized scores, eliminated the effects of age, sex and weight. These statistical techniques were only possible due to the large number of horses studied. Percentiles and standardized scores for LVD, LVS, SW, and PS were calculated by comparing the subject horse to others that were:

The same sex as the subject horse
Measured within 30 days of chronological age of the subject horse
Measured within 1 year of when the subject horse was measured
Within 25 pounds of weight of the subject horse
Percentiles and standardized scores for WEIGHT, HEIGHT and HTWT (HTWT is the product of height times weight) were calculated as above, except without weight restrictions on the comparison group.

Subject comparisons were limited to within ±1 year of the measurement date in order to minimize the possible effects of gradual small changes in calibration, methodology and external variables acting on the subjects. Examples of external variables that may have changed over time and affected measurements include sales preparation techniques of horses at auctions, steroid use, growth hormones, wear and tear on equipment, etc.

Technically, percentiles fail to maintain initial distances between variables. Since most data in natural, biological phenomena is located near the middle of the Gaussian-shaped distribution, measurements in the $50^{th}$ and $52^{nd}$ percentiles are closer in absolute value than those in the $95^{th}$ and $97^{th}$ percentiles. Standardized scores described below maintain the natural spacing between variables, producing a scale-free statistic with a mean of 0, and a standard deviation of 1.

$$\text{Standardized Score} = \frac{\text{Observation} - \text{Mean}}{\text{Standard Deviation}}$$

Standardized scores could be difficult to interpret because, while they generally ranged from −3 to +3, they tended to congregate around zero. It seems easier to understand that a horse is in the $70^{th}$ percentile compared to his peers than to know that his standardized score is 0.55.

Statistical analyses and tables in this text are based on percentiles. The same analyses and tables in terms of standardized scores produced virtually the same results (data not shown).

Example 3

Reproducibility and Sources of Measurement Variability

Variation (or differences) between cardiac measurements is caused by a combination of within- and between-subject variation. Within-subject variation, sometimes called measurement error, indicates how accurately or reproducibly the technician and equipment measures a given variable (hearts and horses are moving targets). Between-subject variation is the range of expected differences among a particular variable in the general population that isn't due to error. Between-subject variation accounted for 84-92% of variation in cardiac measurements in this study, while within-subject variation accounted for 8-16% of variation.

Measurement variability was calculated for LVD, LVS, and SW among 1,464 horses measured in 1999. These cardiac measurements were repeated at least three times within a period of a few minutes. [1,571 horses were measured in 1999. Those excluded from this variability study lacked at least three measurements for LVD, LVS, or SW because of auction conditions, during which the technician may have lacked time to repeat measurements, could not sustain a resting heart rate (or behavioral cooperation), or reported only the average.]

Table 5 summarizes between-subject variation ($s_B$) and within-subject variation ($s_W$) and shows some basic statistical equations used. Column 1 lists the variables studied. Column 2 lists the mean value of each variable among all 1,464 horses in this part of the study. Column 3 lists between-subject variation, which is the standard deviation associated with the mean reported in Column 2. Column 4 lists within-subject variation. Column 5 lists total variation. Column 6 lists the percentage of total variation due to within-subject variation (or measurement error). $S_B^2$ and $S_W^2$, as used in the equations, are mean squared error terms from the between- and within-subject groups studied.

TABLE 5

Summary of Measurement Variability for Combined Sexes
(LVD and LVS units = mm², SW units = mm)

| (1) Variable | (2) Population Mean (n = 1,464) | (3) Between-Subject Variation $\sqrt{s_B^2}$ | (4) Within-Subject Variation $\sqrt{s_W^2}$ | (5) Total Variation $\sqrt{s_W^2 + s_B^2}$ | (6) Pct. of Variation due to Within-Subject Variation $\frac{s_W^2}{s_W^2 + s_B^2} \times 100$ |
|---|---|---|---|---|---|
| LVD | 13,282 | 1,490 | 424 | 1,549 | 7.50% |
| LVS | 4,329 | 496 | 215 | 540 | 15.81% |
| SW | 55.5 | 4.54 | 1.98 | 4.96 | 15.97% |

The within-subject variations listed in Table 5 were used to compute confidence intervals as reported in Table 6, and to answer the following questions:

(1) How accurately did a single cardiac measurement (i.e., not an average of measurements repeated over a period of a few minutes) describe the true value? A statistical solution is to use the "95% confidence interval for a single measurement," as shown in Column 2 of Table 6. In this example, the value was 831 mm² for LVD. This means that there is a 95% probability that the true LVD lies within 831 mm² of a single LVD measurement.

(2) How accurately did the mean of three repeated cardiac measurements over the course of a few minutes describe the true value? A statistical solution is to utilize the "95% confidence interval for repeated measurements," as shown in Column 3 of Table 6. For example, this value was 480 mm² for LVD. This means that there is a 95% probability that the true LVD is within 480 mm² of the mean of three repeated LVD measurements.

(3) How much of a difference between cardiac measurements over some period of time would rule out measurement error as the sole source of the difference? A statistical solution is to use the "95% confidence interval for repeated measurements from two separate dates," as shown in Column 4 of Table 6. For example, this value was 679 mm² for LVD. This means that if the difference between LVD measurements on different dates exceeded 679, then there is a 95% probability that measurement error was not the sole source of that difference.

(4) How much of a difference between repeated cardiac measurements of two different horses would rule out measurement error as the sole source of the difference? A conservative statistical solution is to use the 95% confidence interval just mentioned, as listed in Column 4 of Table 6. For example, this value was 679 mm² for LVD. This means that if the difference between horses' LVDs exceeded 679 mm², then there is a 95% probability that measurement error was not the sole source of that difference.

TABLE 6

95% Confidence Intervals (C.I.) Associated with
Within-Subject Variations Reported in Table 5
(LVD and LVS units = mm², SW units = mm)

| (1) Variable | (2) 95% C.I. for a Single Measurement $1.96 \cdot \sqrt{s_W^2}$ | (3) 95% C.I. for a Measurement Repeated 3 Times Over the Course of a Few Minutes (n = 3) $1.96 \cdot \sqrt{\frac{s_w^2}{n}}$ | (4) 95% C.I. for a Horse Measured on 2 Separate Dates or for Measurements of 2 Different Horses (n = 3) $1.96 \cdot \sqrt{2} \cdot \sqrt{\frac{s_w^2}{n}}$ |
|---|---|---|---|
| LVD | 831 | 480 | 679 |
| LVS | 421 | 243 | 344 |
| SW | 3.9 | 2.3 | 3.2 |

The average percent change in cardiac measurements for horses measured twice within the same month of age was calculated for horses 14-17 months of age. These were the only individual months of age with at least five different horses represented.

The change in the cardiac measurements of these horses fell within the range of expected measurement error described in Table 5. Most change was positive, indicating that growth may have occurred in addition to measurement variation. Measurement variation among horses measured twice within the same month was also influenced by other factors, e.g., some horses were re-measured because the ultrasound technician wasn't satisfied with the initial measurement, likely due to the horse's behavior (i.e., suspected illness, medications, or elevated heart rate after start of exam).

Example 4

Statistical Overview of Cardiac Data—Descriptive Statistics

Means and standard deviations of cardiac raw data for combined sexes are presented in Table 7-Table 8 by months of age.

TABLE 7

Means of Cardiac Measurements for Combined Sexes -
by Months of Age (Total n = 7,434)

| | Number | | | Cardiac Measurement Means | | | | | |
|---|---|---|---|---|---|---|---|---|---|
| Months of Age | of Horses | SPLN | Age (months) | LVD (mm²) | LVS (mm²) | SW (mm) | PS (pct.) | WEIGHT (lbs.) | HEIGHT (hands) |
| 12 | 81 | 171 | 12.5 | 11,534 | 3,823 | 49.4 | 66.82 | 801 | 14.52 |
| 13 | 155 | 174 | 13.5 | 12,025 | 3,982 | 50.7 | 66.86 | 875 | 14.87 |

TABLE 7-continued

Means of Cardiac Measurements for Combined Sexes -
by Months of Age (Total n = 7,434)

| | Number | | | Cardiac Measurement Means | | | | | |
|---|---|---|---|---|---|---|---|---|---|
| Months of Age | of Horses | SPLN | Age (months) | LVD (mm$^2$) | LVS (mm$^2$) | SW (mm) | PS (pct.) | WEIGHT (lbs.) | HEIGHT (hands) |
| 14 | 399 | 175 | 14.6 | 12,362 | 4,038 | 50.9 | 67.32 | 944 | 15.12 |
| 15 | 758 | 176 | 15.6 | 12,395 | 4,024 | 51.1 | 67.52 | 970 | 15.26 |
| 16 | 1,279 | 178 | 16.5 | 12,689 | 4,133 | 51.9 | 67.41 | 986 | 15.37 |
| 17 | 1,196 | 182 | 17.5 | 12,843 | 4,182 | 52.4 | 67.41 | 996 | 15.42 |
| 18 | 856 | 179 | 18.5 | 12,948 | 4,203 | 52.4 | 67.52 | 1,001 | 15.47 |
| 19 | 551 | 186 | 19.4 | 13,285 | 4,330 | 53.5 | 67.36 | 1,005 | 15.51 |
| 20 | 248 | 190 | 20.5 | 13,504 | 4,431 | 53.9 | 67.16 | 1,013 | 15.59 |
| 21 | 337 | 196 | 21.5 | 13,428 | 4,344 | 54.0 | 67.64 | 1,016 | 15.60 |
| 22 | 440 | 201 | 22.5 | 13,633 | 4,411 | 54.7 | 67.64 | 1,026 | 15.64 |
| 23 | 485 | 200 | 23.5 | 13,706 | 4,384 | 54.7 | 68.04 | 1,032 | 15.69 |
| 24 | 333 | 198 | 24.5 | 13,646 | 4,413 | 54.6 | 67.65 | 1,036 | 15.65 |
| 25 | 184 | 201 | 25.4 | 13,803 | 4,409 | 55.2 | 68.08 | 1,046 | 15.77 |
| 26 | 95 | 199 | 26.5 | 13,657 | 4,420 | 54.6 | 67.66 | 1,045 | 15.77 |
| 27 | 37 | 215 | 27.3 | 13,638 | 4,415 | 55.1 | 67.65 | 1,036 | 15.75 |

TABLE 8

Standard Deviations of Cardiac Measurements for Combined Sexes -
by Months of Age Corresponding to Means shown in Table 7
(Total n = 7,434)

| | Number | | | Cardiac Measurement Standard Deviations | | | | | |
|---|---|---|---|---|---|---|---|---|---|
| Months of Age | of Horses | SPLN | Age (months) | LVD (mm$^2$) | LVS (mm$^2$) | SW (mm) | PS (pct.) | WEIGHT (lbs.) | HEIGHT (hands) |
| 12 | 81 | 26.8 | 0.2791 | 1,232 | 424 | 4.09 | 1.989 | 116.2 | 0.592 |
| 13 | 155 | 28.3 | 0.2924 | 1,392 | 505 | 4.46 | 2.206 | 104.6 | 0.493 |
| 14 | 399 | 33.4 | 0.2897 | 1,408 | 519 | 5.12 | 2.329 | 73.9 | 0.394 |
| 15 | 758 | 34.1 | 0.2840 | 1,548 | 553 | 5.16 | 2.223 | 59.6 | 0.357 |
| 16 | 1,279 | 36.5 | 0.2841 | 1,567 | 560 | 5.50 | 2.297 | 50.9 | 0.355 |
| 17 | 1,196 | 38.1 | 0.2902 | 1,541 | 551 | 5.29 | 2.328 | 49.4 | 0.369 |
| 18 | 856 | 37.4 | 0.2783 | 1,595 | 581 | 5.45 | 2.470 | 50.1 | 0.368 |
| 19 | 551 | 39.5 | 0.2800 | 1,504 | 526 | 5.24 | 2.278 | 49.4 | 0.367 |
| 20 | 248 | 38.9 | 0.2898 | 1,347 | 494 | 4.34 | 2.204 | 45.8 | 0.358 |
| 21 | 337 | 45.7 | 0.2908 | 1,459 | 545 | 4.84 | 2.239 | 46.1 | 0.367 |
| 22 | 440 | 46.1 | 0.2760 | 1,404 | 547 | 4.59 | 2.283 | 41.7 | 0.354 |
| 23 | 485 | 44.3 | 0.2889 | 1,366 | 554 | 4.56 | 2.202 | 44.1 | 0.359 |
| 24 | 333 | 46.9 | 0.2965 | 1,493 | 587 | 4.63 | 2.819 | 48.2 | 0.366 |
| 25 | 184 | 45.6 | 0.2886 | 1,519 | 606 | 4.53 | 2.657 | 37.1 | 0.362 |
| 26 | 95 | 46.3 | 0.2887 | 1,410 | 557 | 4.74 | 2.076 | 36.7 | 0.328 |
| 27 | 37 | 48.0 | 0.2498 | 1,590 | 606 | 4.74 | 2.081 | 40.5 | 0.375 |

Figure 4:
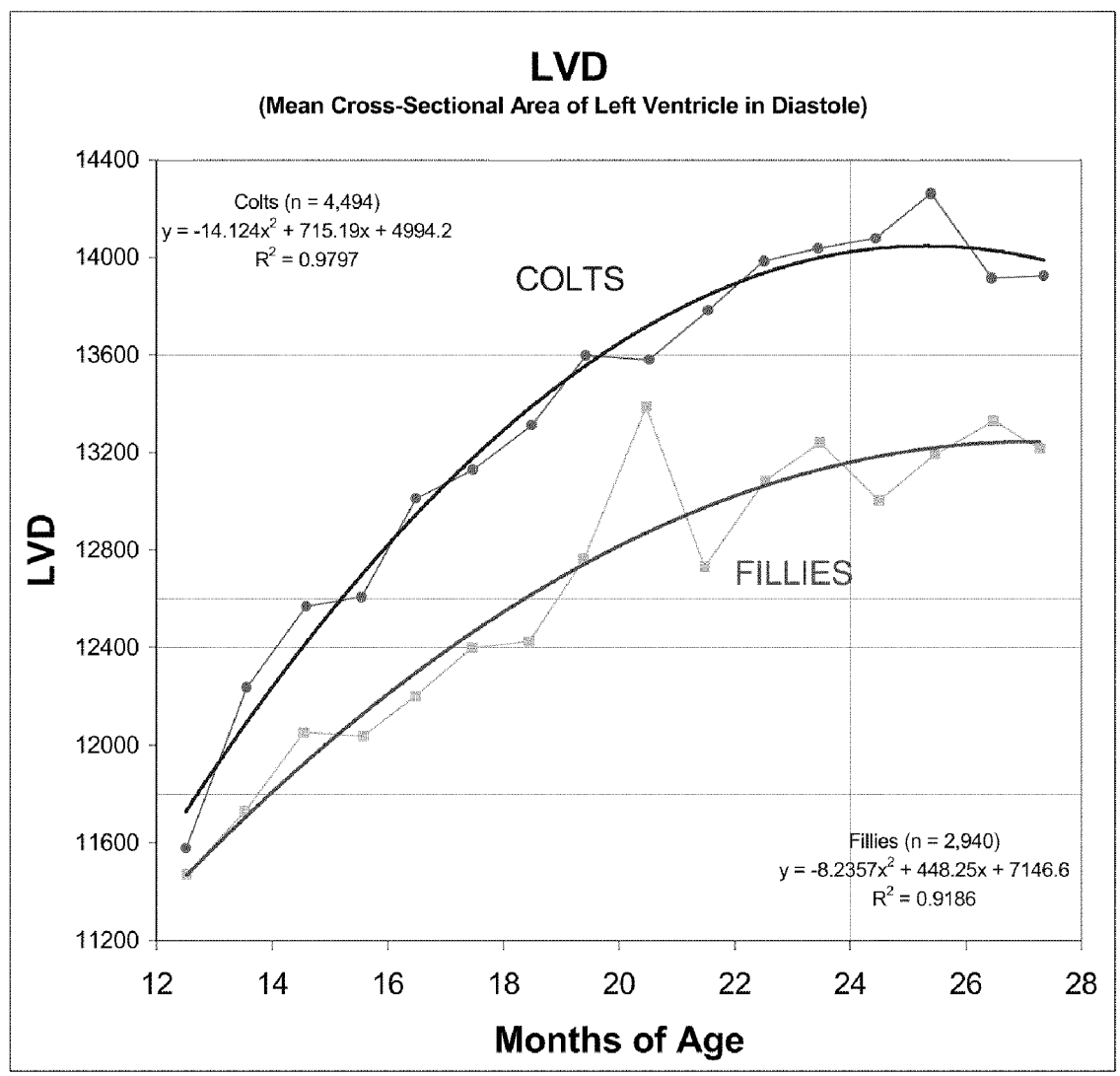
FIG. 4: LVD ($mm^2$) measurements for colts and fillies at ages 12 to 28 months.
Figure 5:
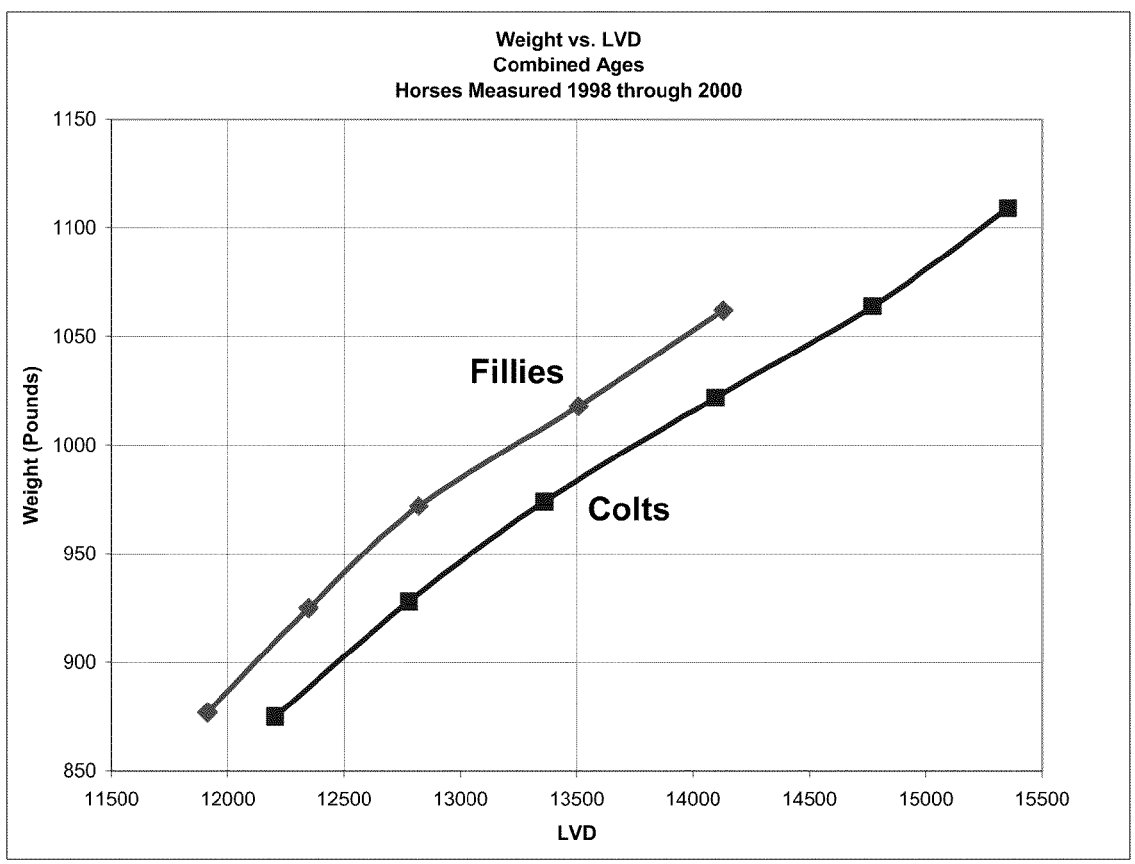
FIG. 5: LVD ($mm^2$) measurements for colts and fillies at weights of 850 to 1150 pounds.
Figure 6:
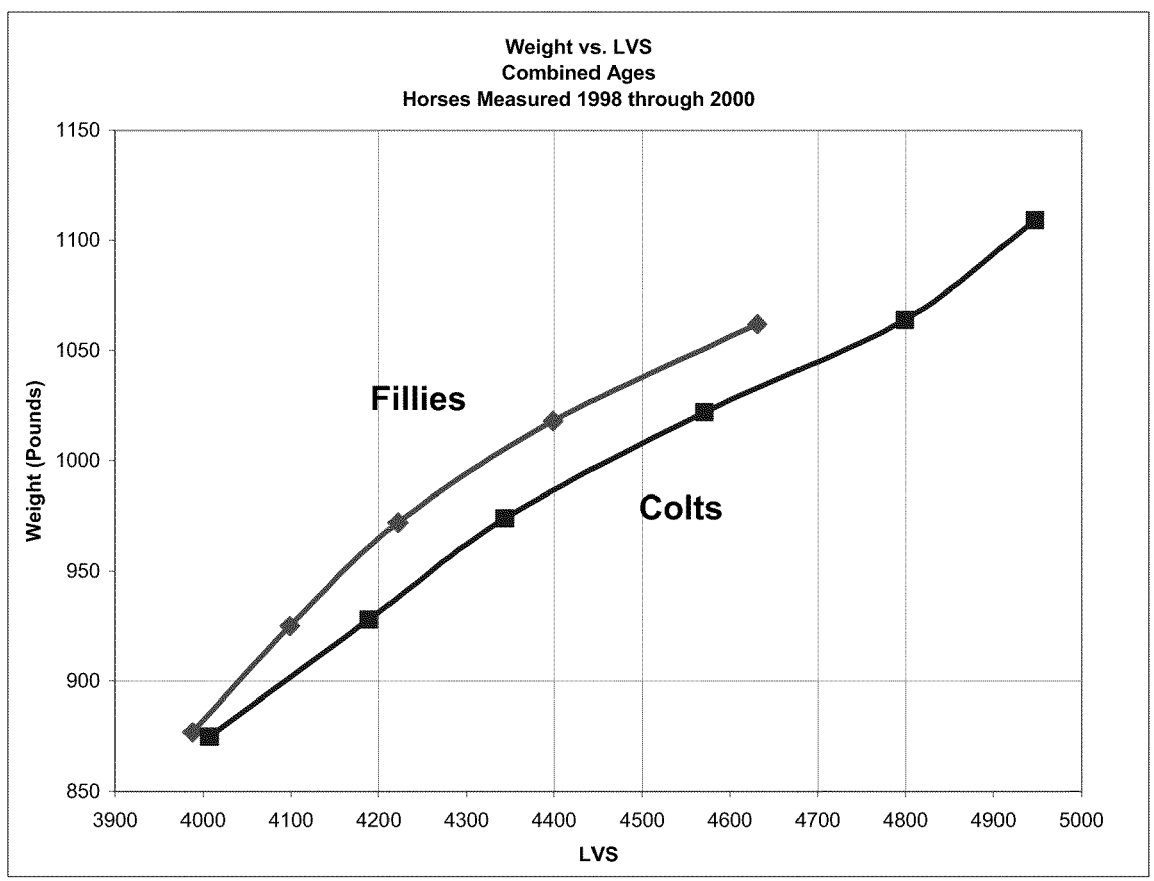
FIG. 6: LVS ($mm^2$) measurements for colts and fillies at weights of 850 to 1150 pounds.
Figure 7:
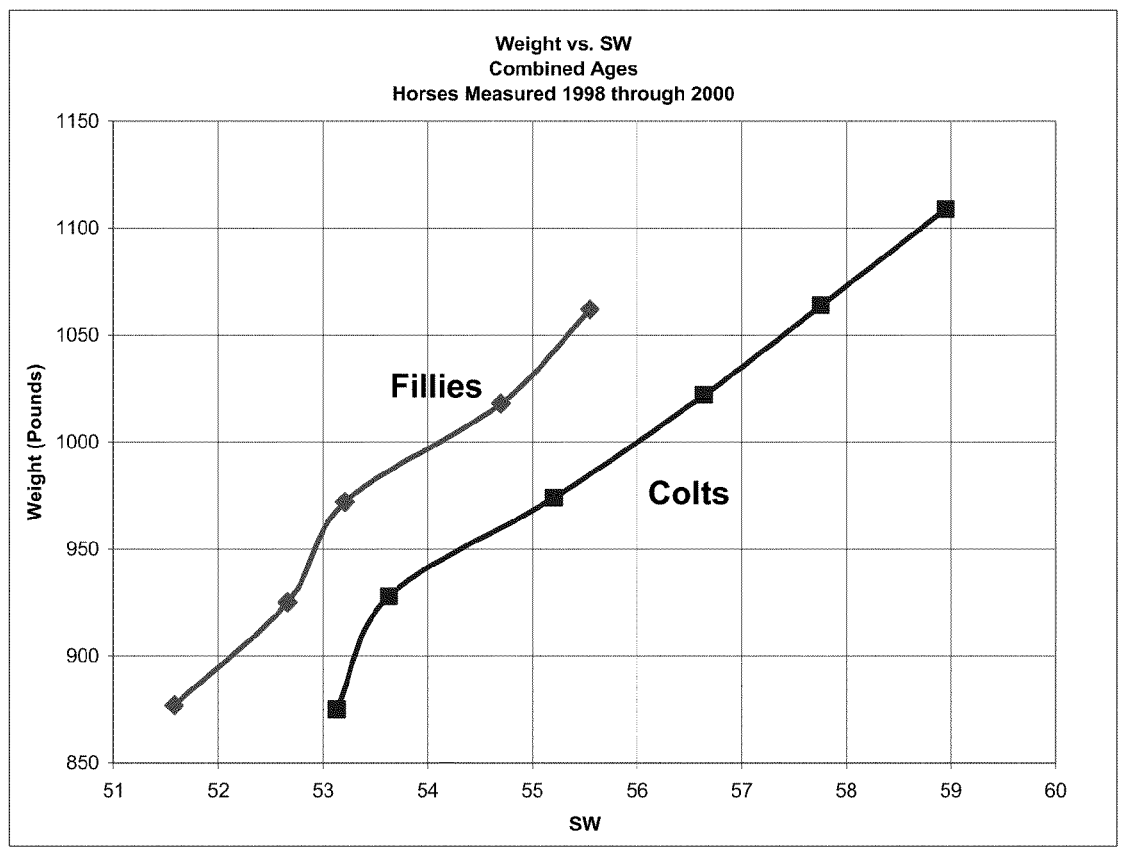
FIG. 7: SW (mm) measurements for colts and fillies at weights of 850 to 1150 pounds.
Figure 8:
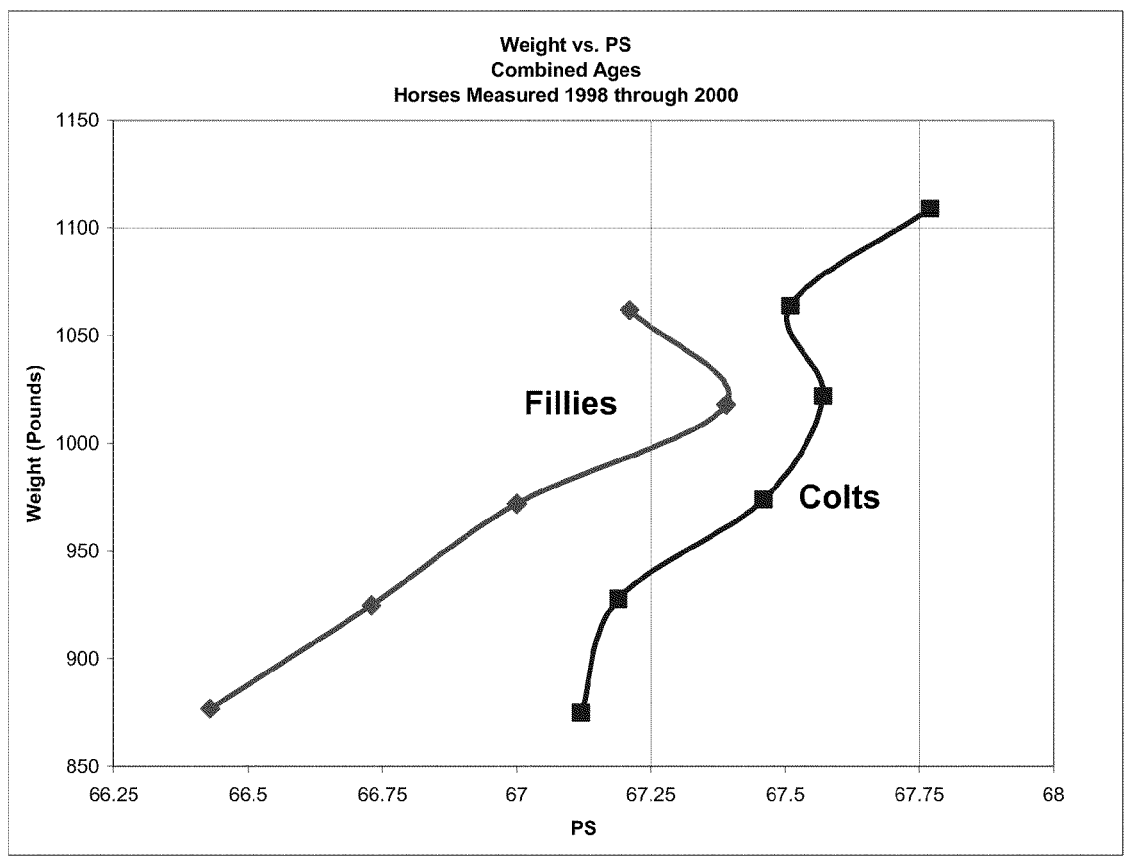
FIG. 8: PS (pct.) measurements for colts and fillies at weights of 850 to 1150 pounds.

Growth Curves—FIG. 4 compares LVD for colts vs. fillies, and is typical of sex-related differences. Most growth curves were described well ($R^2 \geq 0.90$) by second-degree polynomial equations, as shown on the graphs. The growth curves should be limited to application over the period from 12 through 27 months of age for which they were calculated (i.e., not used to estimate average LVD at 32 months of age).

Anomalies appeared in the data patterns of cardiac measurements versus age at 20 and 21 months of age. These horses were primarily measured during October through December, between the timing of select yearling and select two-year-old auctions. Horses often enter training during those interim months. Training regimens, and thus each heart's response to training, likely varied greatly during this time (Young, 1999). Puberty may play a role among fillies at this age. Most horses were measured during this period at private farms, without any pre-selection based on conformation or pedigree. The ratio of colts to fillies (60% colts to 40% fillies) in this study closely matches those at auctions. This ratio may favor colts because breeding farms keep some of the best-bred, best-conformed fillies for their breeding programs. Therefore, relative to auctions, the fillies seen at private farms may be of higher quality, overall, since they may include the best-bred, best-conformed fillies that never make it to auctions.

Figure 9:
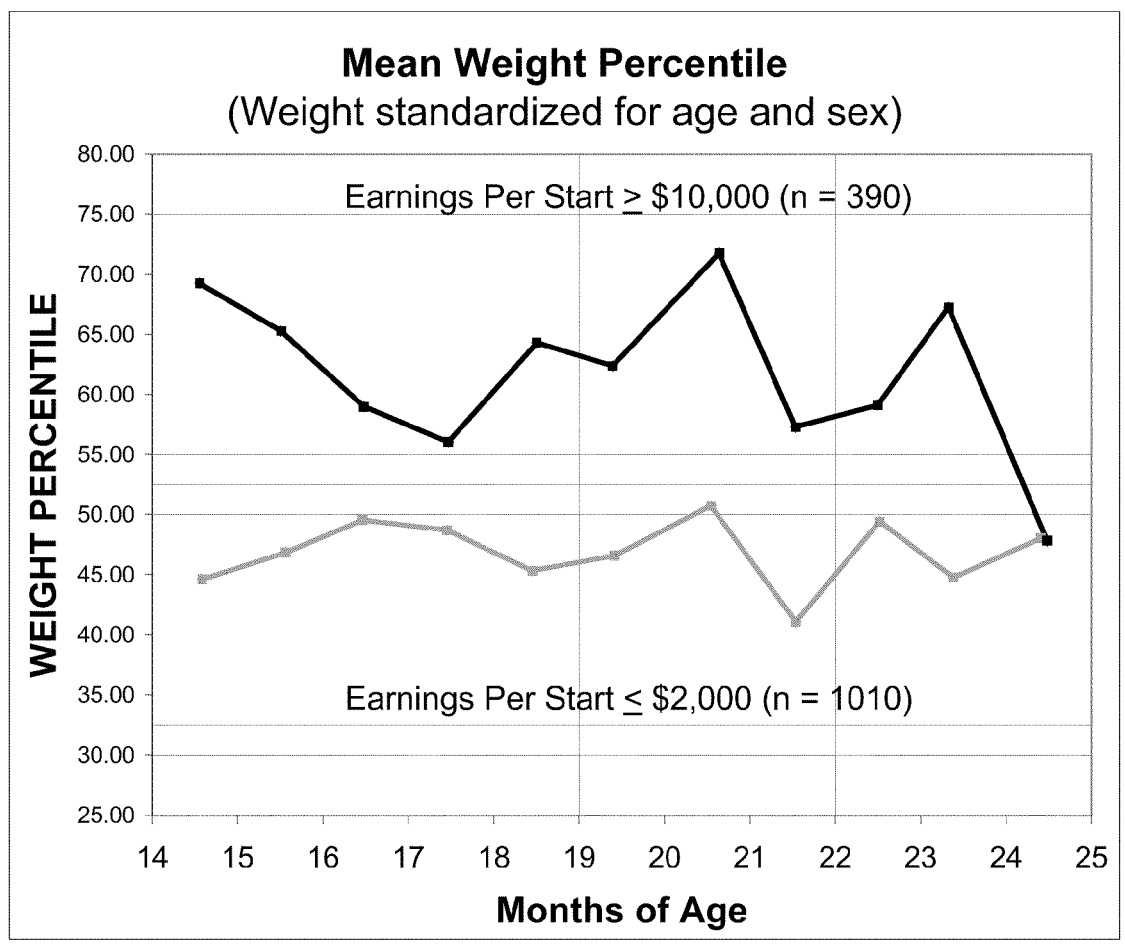
FIG. 9: Mean weight percentiles for high earner and low earner horses at ages 12 to 28 months.
Figure 10:
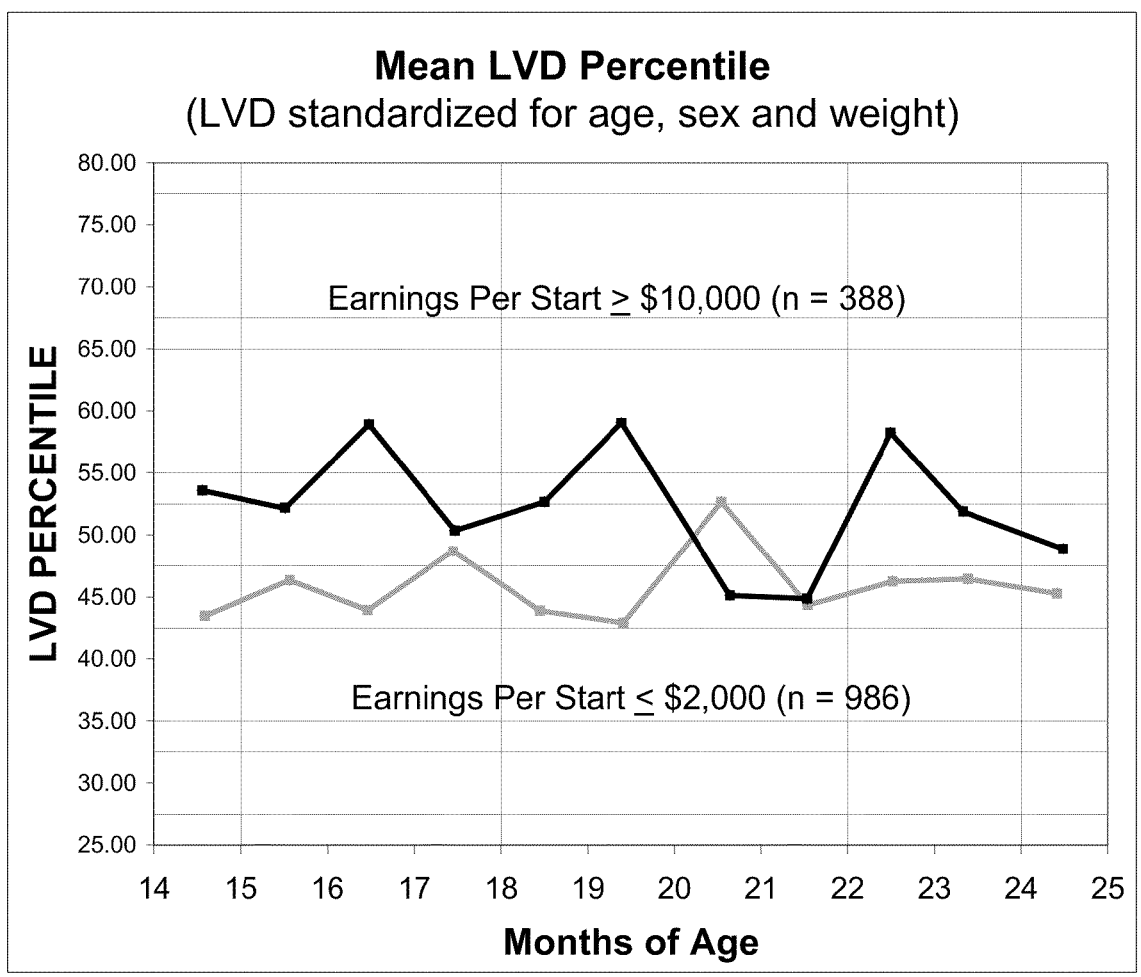
FIG. 10: Mean LVD percentiles for high earner and low earner horses at ages 12 to 28 months.

Among the total population measured, generally, the bigger the horse, the bigger its heart, all else being equal. FIGS. 5-8 provide a visual overview of the relationship between cardiac measurements and the weight of the horse. FIGS. 9-10 compare LVD and WEIGHT percentiles for high earners vs. low earners, and are typical of performance-related differences (except for PS). Not only were future high earners heavier than low earners, but, even when normalized by sex, age and weight, high earners still had higher cardiac measurements. Sample sizes of high earners in these graphs were small at 19 and 20 months of age.

Example 5

Statistical Overview of Cardiac Data—T-Tests

T-tests compared high vs. low earners of combined sexes and ages, using data normalized for sex, age and size. Significant differences (P-values ≦0.0001) existed between high and low earners for all of the cardiac parameters listed in Table 9, except for PS. Stepwise analysis, as discussed in this paper, identified SW or SPLN, LVS and HTWT as the most significant discriminant variables when differentiating between high and low earners. High earners were defined as horses that raced at least three times, with earnings per start of at least $10,000.

TABLE 9

T-tests - Percentiles (Data Adjusted for Age, Sex and Weight) High Earners (Earnings Per Start ≧$10,000) vs. Low Earners (Earnings Per Start ≦$2,000)

| | LOW EARNERS | | | HIGH EARNERS | | | P- |
|---|---|---|---|---|---|---|---|
| VARS | n | Mean | SD | n | Mean | SD | Value |
| LVD | 1061 | 45.93 | 28.61 | 418 | 53.12 | 28.32 | 0.0000 |
| LVS | 1061 | 46.45 | 28.61 | 418 | 52.72 | 28.43 | 0.0001 |
| SW | 1061 | 46.22 | 27.60 | 418 | 53.29 | 27.17 | 0.0000 |
| PS | 1061 | 50.09 | 29.56 | 418 | 49.89 | 29.03 | 0.9050 |
| SPLEEN | 1025 | 42.78 | 22.99 | 405 | 48.87 | 22.71 | 0.0000 |
| WEIGHT | 1091 | 47.25 | 29.40 | 424 | 60.11 | 27.38 | 0.0000 |
| HEIGHT | 1091 | 53.47 | 28.58 | 424 | 65.81 | 26.07 | 0.0000 |
| HTWT | 1091 | 45.32 | 29.02 | 424 | 58.53 | 27.24 | 0.0000 |

T-tests also compared high earner routers vs. high earner sprinters of combined sexes and ages, using data standardized for horses of the same age, sex and size. Significant differences (P-values ≦0.05) existed between high earner routers and sprinters for the cardiac variables of LVD, LVS, WEIGHT, HEIGHT and HTWT, as shown in Table 10. Stepwise analysis, as discussed in this paper, identified LVD, LVS, HTWT and PS as the most significant discriminant variables when differentiating between high earner routers and sprinters. High earner routers raced at least three times at distances of at least 8.5 furlongs, with earnings per start at those route distances of at least $10,000. High earner sprinters raced at least three times at distances below seven furlongs, with earnings per start of at least $10,000 at those sprint distances.

TABLE 10

T-Tests - Percentiles (Data Adjusted for Age, Sex and Weight) High Earner Routers (Raced ≧8.5 Furlongs) vs. High Earner Sprinters (Raced <7 Furlongs)

| | SPRINTERS | | | ROUTERS | | | P- |
|---|---|---|---|---|---|---|---|
| VARS | n | Mean | SD | n | Mean | SD | Value |
| LVD | 180 | 48.68 | 28.69 | 134 | 56.95 | 27.83 | 0.0110 |
| LVS | 180 | 47.68 | 28.31 | 134 | 58.17 | 28.11 | 0.0012 |
| SW | 180 | 52.08 | 27.51 | 134 | 56.60 | 27.27 | 0.1495 |
| PS | 180 | 53.04 | 29.31 | 134 | 47.79 | 27.55 | 0.1085 |
| SPLEEN | 176 | 47.38 | 22.84 | 128 | 50.04 | 23.24 | 0.3207 |
| WEIGHT | 180 | 55.10 | 26.99 | 134 | 64.12 | 24.11 | 0.0024 |
| HEIGHT | 180 | 59.99 | 26.83 | 134 | 69.51 | 24.60 | 0.0014 |
| HTWT | 180 | 52.85 | 27.15 | 134 | 63.06 | 24.50 | 0.0007 |

Example 6

Statistical Overview of Cardiac Data—Standardizing Cardiac Measurements to Eliminate the Effects of Age Sex and Weight The high correlation between age and size vs. most cardiac measurements (see Table 11) was not present among percentiles (see Table 12). Therefore, when looking at horses of different age, sex and size, it is possible to compare their cardiac measurements by standardizing their data (i.e., using percentiles, as described on page 8). To measure the correlation between age and size vs. most cardiac measurements, Pearson correlation coefficients (r) were computed between cardiac measurements for raw data and percentiles (standardized for sex, age and weight). Tests for significance of correlation coefficients produced P-Values <0.0001. Correlation coefficients were squared and multiplied times 100 to compute coefficients of determination (R2), as shown in Table 11-Table 12.

Essentially, due to the standardization of the data, where there was a high degree of correlation throughout the MONTHS column and bottom three rows (WEIGHT, HEIGHT and HTWT) of Table 11, there was little correlation shown in the same column and rows of Table 12 (see shaded areas).

TABLE 11

Coefficients of Determination ($R^2$) (n ranged between 7,288-7,434) Among Raw Data (Unadjusted for Sex, Age and Weight)

| Variables | Coefficients of Determination for Cardiac Measurements-Raw Data | | | | | | | |
|---|---|---|---|---|---|---|---|---|
| | MONTHS | SPLEEN | LVD | LVS | SW | PS | WEIGHT | HEIGHT |
| LVD | 9 | | | | | | | |
| LVS | 6 | | 74 | | | | | |
| SW | 6 | | 70 | 51 | | | | |
| PS | 1 | | 1 | 19 | 1 | | | |
| SPLEEN | 5 | | 33 | 28 | 50 | | | |
| WEIGHT | 22 | 3 | 21 | 14 | 10 | 1 | | |
| HEIGHT | 19 | 3 | 23 | 16 | 13 | 1 | 73 | |
| HTWT | 22 | 3 | 24 | 15 | 12 | 1 | 97 | 86 |

TABLE 12

Coefficients of Determination ($R^2$) (n ranged between 7,288-7,434) Among Percentiles (Standardized for Sex, Age and Weight)

| Variables | Coefficients of Determination for Cardiac Measurements-Percentiles | | | | | | | |
|---|---|---|---|---|---|---|---|---|
| | MONTHS | SPLEEN | LVD | LVS | SW | PS | WEIGHT | HEIGHT |
| LVD | 0 | | | | | | | |
| LVS | 0 | | 62 | | | | | |
| SW | 0 | | 53 | 30 | | | | |
| PS | 0 | | 1 | 20 | 2 | | | |
| SPLEEN | 0 | | 24 | 14 | 35 | 1 | | |
| WEIGHT | 0 | 0 | 0 | 0 | 0 | 0 | | |
| HEIGHT | 0 | 0 | 1 | 0 | 0 | 0 | 67 | |
| HTWT | 0 | 0 | 0 | 0 | 0 | 0 | 96 | 79 |

Example 7

Statistical Overview of Cardiac Data—Covariance Analysis of Means to Assess the Effects of Age and Sex on Cardiac Measurements Analysis of covariance showed that age- and weight-adjusted means for cardiac measurements were significantly different (P-values ≦0.01) between colts and fillies 12 through 27 months old, as shown in Table 13.

TABLE 13

| | Means Adjusted for Age and Weight | | | |
|---|---|---|---|---|
| | LS MEANS | | | |
| VARIABLES | COLTS | FILLIES | P-VALUES | N |
| LVD | 13,315 | 12,832 | 0.0001 | 7,434 |
| LVS | 4,318 | 4,179 | 0.0001 | 7,434 |
| SW | 53.86 | 52.12 | 0.0001 | 7,434 |
| PS | 67.55 | 67.41 | 0.0100 | 7,434 |
| SPLEEN | 193 | 183 | 0.0001 | 7,220 |

Analysis of covariance showed that sex- and weight-adjusted means for cardiac measurements were sometimes significantly different between horses of different months of age. The significance of differences varied depending on the variables studied and the number of months apart. In most cases, significant differences (P-values ≦0.05) were rare or weak when comparing yearlings to yearlings, or two-year-olds to two-year-olds, while differences were significant when comparing yearlings to two-year-olds.

Example 8

Stepwise Discriminant Analysis of the Relationship of Cardiac Measurements to Performance It is impossible to know the level of ability of most horses measured that subsequently never raced, or raced just a couple of times. For this reason, when forming groups of high vs. low earners or routers vs. sprinters, horses used had to have raced at least three times. Raising the minimum number of starts (up to 6) did not improve or weaken discriminant analyses.

Stepwise analysis was conducted for colts, fillies and combined sexes, using percentiles for the variables: LVD, LVS, SW, PS, SPLN and HTWT (HTWT is the product of height times weight).

Stepwise analysis was used to identify statistically significant variables that could differentiate between groups of horses categorized as high and low earners, defined as:

High Earners. Raced at least three times, with earnings per start of at least $10,000.

Low Earners. Raced at least three times, with earnings per start of $2,000 or less.

Among the horses in this study that raced at least three times in North America, 34 percent earned $2,000 or less per start (categorized as "low" earners) and 13 percent earned at least $10,000 per start (categorized as "high" earners). Table 2 provides average worldwide performance statistics for the Thoroughbred breed.

For high vs. low earners, stepwise analysis identified the following significant variables (listed in order of statistical significance):

Combined Sexes. HTWT, SW or SPLN, LVS
Colts. HTWT, SW or SPLN
Fillies. HTWT, SW or SPLN Stepwise analysis was used to identify statistically significant variables that could differentiate between groups of horses categorized as high earner sprinters and high earner routers, defined as:

High Earner Sprinters. Raced at least 3 times at distances <7.0 furlongs, earned at least $10,000 per start at distances <7.0 furlongs, and earned less than $2,000 per start at distances ≧8.5 furlongs.

High Earner Routers. Raced at least 3 times at distances ≧8.5 furlongs, and earned at least $10,000 per start at distances ≧8.5 furlongs.

For high earner sprinters vs. high earner routers, stepwise analysis identified the following significant variables (listed in order of statistical significance):

Combined Sexes. HTWT, LVS
Colts. LVD, HTWT
Fillies. PS, HTWT

Example 9

Multivariate Discriminant Analysis of the Relationship of Measurements to Performance Discriminant analysis was used to classify high earners vs. low earners, and high earner routers vs. high earner sprinters, as defined in the stepwise analysis section.

Discriminant results were based on a classification threshold of 50%. A classification threshold is the minimum acceptable probability (as defined by the model user) required to classify a horse into a particular group. Thus, no horse was classified into a group unless the models assigned it at least a 50% probability of belonging to that group. Generally, the higher the threshold, the better the models performed (i.e., a horse with a 70% high earner probability was more likely to be a high earner than a horse with a lower probability. As the threshold increases for a particular group, the models generally misclassify more members of that group. At public auctions, a high "high earner" threshold would minimize the chances of buying poor performers (Type II errors), while increasing the chances of rejecting good performers (Type I errors).

Z-statistics were computed to determine the reliability of discriminant results using the formula below (shown for high earners):

$$Z_H = \frac{P_{H_{post}} - P_{H_{pre}}}{\sqrt{\frac{P_{H_{pre}} \cdot (1 - P_{H_{pre}})}{N_{CH_{post}}}}}$$

Where: $N_{Hpre}$=Number of high earners in model
$N_{Tpre}$=Total number of horses in model
$N_{HCCpost}$=Number of high earners correctly classified by model
$N_{CHpost}$=Number of horses classified as high earners by model
$P_{Hpre}$=Pre-model probability ($N_{Hpre}/N_{Tpre}$)
$P_{Hpost}$=Post-model probability ($N_{HCCpost}/N_{CHpost}$)

P-values associated with the Z-statistics were reported in place of Z-statistics (Table 14-Table 25).

The model parameters were:

Horses had to be born by 1997 (so would have racing data through three-year-old year)

Horses had to have at least 3 starts (i.e., sound enough to race multiple times)

Two types of discriminant analyses, called blind and non-blind tests, were conducted for each model.

Non-Blind Test. A non-blind test is one in which the horses classified by a model were used to create the model. Thus, the models "saw" those horses before. A non-blind test is the best-case scenario of how well a model performs.

Blind Test. A blind-test is one in which the horses classified by a model were not used to create the model. Thus, the models did not "see" those horses before.

Three tables were used to summarize each discriminant analysis in terms of blind and non-blind tests. The first table presents non-blind test results based on all horses available for the study. The second table presents non-blind test results based on horses with names beginning with the letters A-M. The third table presents blind-test results, for which the A-M model was used to classify horses with names beginning with the letters N-Z, which the models hadn't seen previously. Each table presents summary statistics as described below:

Pre-Model Probability. Discriminating between two groups (A and B), the pre-model probability is the ratio of all Group A or Group B horses to the total number of horses in the model. This is the probability, using a random selection technique without statistically created models, of correctly classifying a Group A or Group B horse. This probability is shown as a Ratio and a Percent. For example, if there are 7 Group A horses and 93 Group B horses, there is a 7% probability of randomly selecting a Group A horse. For Group A horses, this would be shown as a ratio of 7/100 and as a percent of 7.00.

Post-Model Probability. Discriminating between two groups (A and B) the post-model probability is the ratio of Group A or Group B horses correctly classified by the models to the total number of horses classified by the statistically created models as Group A or Group B horses. This is the probability with discriminant models of correctly classifying Group A or Group B horses. Using the example above, a discriminant model classifying the same 100 horses might classify 25 horses into Group A, of which 5 horses actually belonged to Group A. In this case, the ratio for Group A horses would be 5/25, or 20 percent. Thus, in this example, the discriminant models improved the odds of correctly identifying Group A horses from 7% without models to 20% with models. Likewise, they improved the odds of correctly classifying Group B horses from 93% without models to 73/75, or 97.3% with models.

P-value. The P-value was listed corresponding to the Z-statistic computed for each model.

The variables HTWT, SW, and LVS, as identified by stepwise analysis, were used in the following high earner vs. low earner discriminant models, e.g., Tables 14-25. The predictive results of the blind and non-blind tests were similar. Results showed that as long as data was first standardized (using percentiles) for each subject's sex, age and size, each subject's data could be compared with data from subjects of different sex, age and size. This made the combined sexes discriminant models just as powerful as separate colt and filly models.

Further comparisons of earnings groups, including $10,000+ earnings per start vs. less than $7,500-earnings per start produced similar results. Thus, the models, using the same independent variables, successfully differentiated between stakes- and allowance-caliber horses, as well as between stakes- and claiming-caliber horses.

Horses generally earned more and raced less frequently as the probability of being high earners, as assigned by the discriminant model, increased.

Table 14-Table 16 summarize discriminant results for non-blind and blind tests of high earners and low earners, comprised of colts and fillies combined, that had raced at least three times (i.e., had three "starts"). High earners earned at least $10,000 per start and low earners earned $2,000 or less per start. The improvement associated with discriminant modeling was statistically significant for both high and low earners for all groups studied (P-values ≦0.0027).

Non-Blind A-Z. Table 14 shows that among 1,479 total horses, non-blind discriminant models improved the odds of correctly classifying high earners from 28.26% without models to 37.32% with models. They improved the odds of correctly classifying low earners from 71.74% without models to 79.57% with models. The improvement associated with discriminant modeling was statistically significant for both high and low earners (P-values <0.0001).

TABLE 14

Discriminant Model Results - High Earners vs. Low Earners Non-Blind Tests -- Combined Sexes - Names Starting with Letters A-Z

| Category | Pre-Model Probability | | Post-Model Probability | | P-Value |
|---|---|---|---|---|---|
| | Ratio | Pct. | Ratio | Pct. | |
| High Earners | 418/1479 | 28.26 | 256/686 | 37.32 | 0.0000 |
| Low Earners | 1061/1479 | 71.74 | 631/793 | 79.57 | 0.0000 |

Non-Blind A-M. Table 15 shows that among horses with names beginning with the letters A-M, non-blind discriminant models improved the odds of correctly classifying high earners from 27.75% without models to 37.65% with models. They improved the odds of correctly classifying low earners from 72.25% without models to 80.80% with models. The improvement associated with discriminant modeling was statistically significant for both high and low earners (P-values <0.0001).

TABLE 15

Discriminant Model Results - High Earners vs. Low Earners Non-Blind Tests -- Combined Sexes - Names Starting with Letters A-M

| Category | Pre-Model Probability | | Post-Model Probability | | P-Value |
|---|---|---|---|---|---|
| | Ratio | Pct. | Ratio | Pct. | |
| High Earners | 245/883 | 27.75 | 154/409 | 37.65 | 0.0000 |
| Low Earners | 638/883 | 72.25 | 383/474 | 80.80 | 0.0000 |

Blind N-Z. Table 16 shows that among horses with names beginning with the letters N-Z, blind discriminant models based on the A-M horses improved the odds of correctly classifying high earners from 29.03% without models to 37.77% with models. They improved the odds of correctly classifying low earners from 70.97% without models to 78.62% with models. The improvement associated with discriminant modeling was statistically significant for both high and low earners (P-values ≦0.0027).

TABLE 16

Discriminant Model Results - High Earners vs. Low Earners Blind Test -- Combined Sexes - Names Starting with Letters N-Z

| Category | Pre-Model Probability | | Post-Model Probability | | P-Value |
|---|---|---|---|---|---|
| | Ratio | Pct. | Ratio | Pct. | |
| High Earners | 173/596 | 29.03 | 105/278 | 37.77 | 0.0013 |
| Low Earners | 423/596 | 70.97 | 250/318 | 78.62 | 0.0027 |

Table 17-Table 19 summarize discriminant results for high vs. low earners among colts. Table 17 shows that among 880 colts, non-blind discriminant models improved the odds of correctly classifying high earners from 26.70% without models to 34.96% with models. They improved the odds of correctly classifying low earners from 73.30% without models to 80.47% with models. The improvement associated with discriminant modeling was statistically significant for both high and low earners (P-values $\leq 0.0004$).

TABLE 17

Discriminant Model Results - High Earners vs. Low Earners Non-Blind Tests - Colts - Names Starting with Letters A-Z

| Category | Pre-Model Probability | | Post-Model Probability | | P-Value |
|---|---|---|---|---|---|
| | Ratio | Pct. | Ratio | Pct. | |
| High Earners | 235/880 | 26.70 | 143/409 | 34.96 | 0.0002 |
| Low Earners | 645/880 | 73.30 | 379/471 | 80.47 | 0.0004 |

Non-Blind A-M. Table 18 shows that among colts with names beginning with the letters A-M, non-blind discriminant models improved the odds of correctly classifying high earners from 26.47% without models to 33.33% with models. They improved the odds of correctly classifying low earners from 73.53% without models to 79.51% with models. The improvement associated with discriminant modeling was statistically significant for both high and low earners (P-values $\leq 0.0226$).

TABLE 18

Discriminant Model Results - High Earners vs. Low Earners Non-Blind Tests - Colts - Names Starting with Letters A-M

| Category | Pre-Model Probability | | Post-Model Probability | | P-Value |
|---|---|---|---|---|---|
| | Ratio | Pct. | Ratio | Pct. | |
| High Earners | 140/529 | 26.47 | 82/246 | 33.33 | 0.0147 |
| Low Earners | 389/529 | 73.53 | 225/283 | 79.51 | 0.0226 |

Blind N-Z. Table 19 shows that among colts with names beginning with the letters N-Z, blind discriminant models based on the A-M horses improved the odds of correctly classifying high earners from 27.07% without models to 38.41% with models. They improved the odds of correctly classifying low earners from 72.93% without models to 82.89% with models. The improvement associated with discriminant modeling was statistically significant for both high and low earners (P-values $\leq 0.0022$).

TABLE 19

Discriminant Model Results - High Earners vs. Low Earners Blind Test - Colts - Names Starting with Letters N-Z

| Category | Pre-Model Probability | | Post-Model Probability | | P-Value |
|---|---|---|---|---|---|
| | Ratio | Pct. | Ratio | Pct. | |
| High Earners | 95/351 | 27.07 | 63/164 | 38.41 | 0.0011 |
| Low Earners | 256/351 | 72.93 | 155/187 | 82.89 | 0.0022 |

Table 20-Table 22 summarize discriminant results for high vs. low earners among fillies.

Non-Blind A-Z. Table 20 shows that among 599 fillies, non-blind discriminant models improved the odds of correctly classifying high earners from 30.55% without models to 42.22% with models. They improved the odds of correctly classifying low earners from 69.45% without models to 79.03% with models. The improvement associated with discriminant modeling was statistically significant for both high and low earners (P-values $\leq 0.0002$).

TABLE 20

Discriminant Model Results - High Earners vs. Low Earners Non-Blind Tests - Fillies - Names Starting with Letters A-Z

| Category | Pre-Model Probability | | Post-Model Probability | | P-Value |
|---|---|---|---|---|---|
| | Ratio | Pct. | Ratio | Pct. | |
| High Earners | 183/599 | 30.55 | 114/270 | 42.22 | 0.0000 |
| Low Earners | 416/599 | 69.45 | 260/329 | 79.03 | 0.0002 |

Non-Blind A-M. Table 21 shows that among fillies with names beginning with the letters A-M, non-blind discriminant models improved the odds of correctly classifying high earners from 29.66% without models to 44.16% with models. They improved the odds of correctly classifying low earners from 70.34% without models to 81.50% with models. The improvement associated with discriminant modeling was statistically significant for both high and low earners (P-values $\leq 0.0005$).

TABLE 21

Discriminant Model Results - High Earners vs. Low Earners Non-Blind Tests - Fillies - Names Starting with Letters A-M

| Category | Pre-Model Probability | | Post-Model Probability | | P-Value |
|---|---|---|---|---|---|
| | Ratio | Pct. | Ratio | Pct. | |
| High Earners | 105/354 | 29.66 | 68/154 | 44.16 | 0.0001 |
| Low Earners | 249/354 | 70.34 | 163/200 | 81.50 | 0.0005 |

Blind N-Z. Table 22 shows that among fillies with names beginning with the letters N-Z, blind discriminant models based on the A-M horses improved the odds of correctly classifying high earners from 31.84% without models to 39.50% with models. They improved the odds of correctly classifying low earners from 68.16% without models to 75.40% with models. The improvement associated with discriminant modeling was not statistically significant for high or low earners (P-values $\leq 0.0819$).

TABLE 22

Discriminant Model Results - High Earners vs. Low Earners
Blind Test - Fillies - Names Starting with Letters N-Z

| Category | Pre-Model Probability | | Post-Model Probability | | P-Value |
|---|---|---|---|---|---|
| | Ratio | Pct. | Ratio | Pct. | |
| High Earners | 78/245 | 31.84 | 47/119 | 39.50 | 0.0735 |
| Low Earners | 167/245 | 68.16 | 95/126 | 75.40 | 0.0819 |

The variables HTWT and LVS, as identified by stepwise analysis, were used in the high earner routers vs. sprinters discriminant models for combined sexes (see Exhibits PM05290204 & PM05290205).

Table 23-Table 25 summarize discriminant results for high earner routers vs. sprinters. Table 23 shows that among 314 high earner horses, non-blind discriminant models improved the odds of correctly classifying routers from 42.68% without models to 55.03% with models. They improved the odds of correctly classifying sprinters from 57.32% without models to 68.48% with models. The improvement associated with discriminant modeling was statistically significant for both routers and sprinters (P-values ≦0.0037).

TABLE 23

Discriminant Model Results - High Earner Routers
vs. High Earner Sprinters Non-Blind Tests -- Combined
Sexes -- Names Starting with Letters A-Z

| Category | Pre-Model Probability | | Post-Model Probability | | P-Value |
|---|---|---|---|---|---|
| | Ratio | Pct. | Ratio | Pct. | |
| Routers | 134/314 | 42.68 | 82/149 | 55.03 | 0.0023 |
| Sprinters | 180/314 | 57.32 | 113/165 | 68.48 | 0.0037 |

Non-Blind A-M. Table 24 shows that among high earner horses with names beginning with the letters A-M, non-blind discriminant models improved the odds of correctly classifying routers from 37.78% without models to 51.85% with models. They improved the odds of correctly classifying sprinters from 62.22% without models to 73.74% with models. The improvement associated with discriminant modeling was statistically significant for both routers and sprinters (P-values ≦0.0183).

TABLE 24

Discriminant Model Results - High Earner Routers
vs. High Earner Sprinters Non-Blind Tests -- Combined
Sexes - Names Starting with Letters A-M

| Category | Pre-Model Probability | | Post-Model Probability | | P-Value |
|---|---|---|---|---|---|
| | Ratio | Pct. | Ratio | Pct. | |
| Routers | 68/180 | 37.78 | 42/81 | 51.85 | 0.0091 |
| Sprinters | 112/180 | 62.22 | 73/99 | 73.74 | 0.0183 |

Blind N-Z. Table 25 shows that among high earner horses with names beginning with the letters N-Z, blind discriminant models based on the A-M horses improved the odds of correctly classifying routers from 49.25% without models to 60.94% with models. They improved the odds of correctly classifying sprinters from 50.75% without models to 61.43% with models. The improvement associated with discriminant modeling was not statistically significant for routers or sprinters (P-values ≦0.0735).

TABLE 25

Discriminant Model Results - High Earner Routers
vs. High Earner Sprinters Blind Test -- Combined
Sexes - Names Starting with Letters N-Z

| Category | Pre-Model Probability | | Post-Model Probability | | P-Value |
|---|---|---|---|---|---|
| | Ratio | Pct. | Ratio | Pct. | |
| Routers | 66/134 | 49.25 | 39/64 | 60.94 | 0.0588 |
| Sprinters | 68/134 | 50.75 | 43/70 | 61.43 | 0.0735 |

The variables HTWT, SPLEEN and LVS, as identified by stepwise analysis, were used in the following high earner vs. low earner discriminant models, e.g., Tables 26.

Table 26-Table 28 summarize discriminant results for non-blind and blind tests of high earners and low earners, comprised of colts and fillies combined, that had raced at least three times (i.e., had three "starts"). High earners earned at least $10,000 per start and low earners earned $2,000 or less per start. The improvement associated with discriminant modeling was statistically significant for both high and low earners for all groups studied (P-values ≦0.0002).

Non-Blind A-Z. Table 26 shows that among 1,430 total horses, non-blind discriminant models improved the odds of correctly classifying high earners from 28.32% without models to 37.78% with models. They improved the odds of correctly classifying low earners from 71.68% without models to 79.95% with models. The improvement associated with discriminant modeling was statistically significant for both high and low earners (P-values <0.0001).

TABLE 26

Discriminant Model Results - High Earners vs. Low Earners Non-Blind
Tests -- Combined Sexes - Names Starting with Letters A-Z

| Category | Pre-Model Probability | | Post-Model Probability | | P-Value |
|---|---|---|---|---|---|
| | Ratio | Pct. | Ratio | Pct. | |
| High Earners | 405/1430 | 28.32 | 252/667 | 37.78 | 0.0000 |
| Low Earners | 1025/1430 | 71.68 | 610/763 | 79.95 | 0.0000 |

Non-Blind A-M. Table 27 shows that among horses with names beginning with the letters A-M, non-blind discriminant models improved the odds of correctly classifying high earners from 27.87% without models to 37.47% with models. They improved the odds of correctly classifying low earners from 72.13% without models to 80.39% with models. The improvement associated with discriminant modeling was statistically significant for both high and low earners (P-values ≦0.0001).

TABLE 27

Discriminant Model Results - High Earners vs. Low Earners Non-Blind
Tests -- Combined Sexes - Names Starting with Letters A-M

| Category | Pre-Model Probability | | Post-Model Probability | | P-Value |
|---|---|---|---|---|---|
| | Ratio | Pct. | Ratio | Pct. | |
| High Earners | 238/854 | 27.87 | 148/395 | 37.47 | 0.0000 |
| Low Earners | 616/854 | 72.13 | 369/459 | 80.39 | 0.0001 |

Blind N-Z. Table 28 shows that among horses with names beginning with the letters N-Z, blind discriminant models based on the A-M horses improved the odds of correctly classifying high earners from 28.99% without models to 38.21% with models. They improved the odds of correctly classifying low earners from 71.01% without models to 79.73% with models. The improvement associated with discriminant modeling was statistically significant for both high and low earners (P-values $\leq 0.0009$).

TABLE 28

Discriminant Model Results - High Earners vs. Low Earners Blind Test -- Combined Sexes - Names Starting with Letters N-Z

| Category | Pre-Model Probability | | Post-Model Probability | | P-Value |
|---|---|---|---|---|---|
| | Ratio | Pct. | Ratio | Pct. | |
| High Earners | 167/576 | 28.99 | 107/280 | 38.21 | 0.0007 |
| Low Earners | 409/576 | 71.01 | 236/296 | 79.73 | 0.0009 |

Colts

Table 29-Table 31 summarize discriminant results for high vs. low earners among colts.

Non-Blind A-Z. Table 29 shows that among 859 colts, non-blind discriminant models improved the odds of correctly classifying high earners from 26.66% without models to 34.89% with models. They improved the odds of correctly classifying low earners from 73.34% without models to 80.75% with models. The improvement associated with discriminant modeling was statistically significant for both high and low earners (P-values $\leq 0.0004$).

TABLE 29

Discriminant Model Results - High Earners vs. Low Earners Non-Blind Tests - Colts - Names Starting with Letters A-Z

| Category | Pre-Model Probability | | Post-Model Probability | | P-Value |
|---|---|---|---|---|---|
| | Ratio | Pct. | Ratio | Pct. | |
| High Earners | 229/859 | 26.70 | 142/407 | 34.89 | 0.0002 |
| Low Earners | 630/859 | 73.34 | 365/452 | 80.75 | 0.0004 |

Non-Blind A-M. Table 30 shows that among colts with names beginning with the letters A-M, non-blind discriminant models improved the odds of correctly classifying high earners from 26.45% without models to 34.58% with models. They improved the odds of correctly classifying low earners from 73.55% without models to 80.58% with models. The improvement associated with discriminant modeling was statistically significant for both high and low earners (P-values $\leq 0.0078$).

TABLE 30

Discriminant Model Results - High Earners vs. Low Earners Non-Blind Tests - Colts - Names Starting with Letters A-M

| Category | Pre-Model Probability | | Post-Model Probability | | P-Value |
|---|---|---|---|---|---|
| | Ratio | Pct. | Ratio | Pct. | |
| High Earners | 137/518 | 26.45 | 83/240 | 34.58 | 0.0042 |
| Low Earners | 381/518 | 73.55 | 224/278 | 80.58 | 0.0078 |

Blind N-Z. Table 31 shows that among colts with names beginning with the letters N-Z, blind discriminant models based on the A-M horses improved the odds of correctly classifying high earners from 26.98% without models to 36.65% with models. They improved the odds of correctly classifying low earners from 73.02% without models to 81.67% with models. The improvement associated with discriminant modeling was statistically significant for both high and low earners (P-values $\leq 0.0091$).

TABLE 31

Discriminant Model Results - High Earners vs. Low Earners Blind Test - Colts - Names Starting with Letters N-Z

| Category | Pre-Model Probability | | Post-Model Probability | | P-Value |
|---|---|---|---|---|---|
| | Ratio | Pct. | Ratio | Pct. | |
| High Earners | 92/341 | 26.98 | 59/161 | 36.65 | 0.0058 |
| Low Earners | 249/341 | 73.02 | 147/180 | 81.67 | 0.0091 |

Fillies

Table 32-Table 34 summarize discriminant results for high vs. low earners among fillies.

Non-Blind A-Z. Table 32 shows that among 571 fillies, non-blind discriminant models improved the odds of correctly classifying high earners from 30.82% without models to 42.01% with models. They improved the odds of correctly classifying low earners from 69.18% without models to 79.14% with models. The improvement associated with discriminant modeling was statistically significant for both high and low earners (P-values $\leq 0.0002$).

TABLE 32

Discriminant Model Results - High Earners vs. Low Earners Non-Blind Tests - Fillies - Names Starting with Letters A-Z

| Category | Pre-Model Probability | | Post-Model Probability | | P-Value |
|---|---|---|---|---|---|
| | Ratio | Pct. | Ratio | Pct. | |
| High Earners | 176/571 | 30.82 | 113/269 | 42.01 | 0.0001 |
| Low Earners | 395/571 | 69.18 | 239/302 | 79.14 | 0.0002 |

Non-Blind A-M. Table 33 shows that among fillies with names beginning with the letters A-M, non-blind discriminant models improved the odds of correctly classifying high earners from 30.06% without models to 43.05% with models. They improved the odds of correctly classifying low earners from 69.94% without models to 80.54% with models. The improvement associated with discriminant modeling was statistically significant for both high and low earners (P-values $\leq 0.0017$).

TABLE 33

Discriminant Model Results - High Earners vs. Low Earners Non-Blind Tests - Fillies - Names Starting with Letters A-M

| Category | Pre-Model Probability | | Post-Model Probability | | P-Value |
|---|---|---|---|---|---|
| | Ratio | Pct. | Ratio | Pct. | |
| High Earners | 101/336 | 30.06 | 65/151 | 43.05 | 0.0005 |
| Low Earners | 235/336 | 69.94 | 149/185 | 80.54 | 0.0017 |

Blind N-Z. Table 34 shows that among fillies with names beginning with the letters N-Z, blind discriminant models based on the A-M horses improved the odds of correctly classifying high earners from 31.91% without models to 40.34% with models. They improved the odds of correctly classifying low earners from 68.09% without models to 76.72% with models. The improvement associated with discriminant modeling was statistically significant for both high and low earners (P-values ≦0.0488).

TABLE 34

Discriminant Model Results - High Earners vs. Low Earners
Blind Test - Fillies - Names Starting with Letters N-Z

| Category | Pre-Model Probability | | Post-Model Probability | | P-Value |
|---|---|---|---|---|---|
| | Ratio | Pct. | Ratio | Pct. | |
| High Earners | 75/235 | 31.91 | 48/119 | 40.34 | 0.0488 |
| Low Earners | 160/235 | 68.09 | 89/116 | 76.72 | 0.0455 |

Example 10

Chi-Square Analysis of Performance vs. Heart Size and Physical Size

The statistical methods described to this point, and which have shown the predictive nature of cardiac measurements, are perhaps less intuitive than the following examples. Once the key variables of HTWT (the product of height times weight—used as a measure of physical size), LVD, LVS, PS, SPLN, and SW were standardized for age, sex and weight, on a scale from 0 (small) to 100 (large), groups of horses based on these variables could be created. For example, groups of horses could be created with above or below average LVD, or horses could be grouped into quartiles (i.e., from the bottom 25% to the top 25%) based on specific heart measurements or physical size. Questions such as: "Was there as high a percentage of high earners among horses with below average LVD as among horses with above average LVD?" could then be answered.

Table 35 shows the percentage of horses that earned at least $10,000 per racing start among horses grouped by physical size and heart size. Overall, 13.3 percent of the horses in this study's sample earned at least $10,000 per start.

TABLE 35

Percentage of Horses that Earned at least $10,000 Per Start
Based on Percentiles for Individual Variables

| | Percentiles | | | |
|---|---|---|---|---|
| | 0-25% | 25-50% | 50-75% | 75-100% |
| HTWT | 7.6 | 12.8 | 14.5 | 17.8 |
| LVD | 11.6 | 11.1 | 13.4 | 17.5 |
| LVS | 11.4 | 11.8 | 13.9 | 16.3 |
| SW | 10.8 | 13.1 | 13.1 | 16.3 |
| PS | 14.3 | 11.4 | 14.0 | 13.3 |
| Average* | 10.4 | 12.2 | 13.7 | 17.0 |

*Average was calculated excluding PS, which wasn't usually predictive.

Table 35 shows that as physical size and heart size measurements increased, except for PS, so did the percentage of high earners. This table shows that 17.8% of horses with HTWT in the 75-100% percentile range earned at least $10,000 per start. The percentage of horses that earned at least $10,000 per start was below average (13.3% was average for all horses studied) for groups with cardiac variables below the 50$^{th}$ percentile. Horses with cardiac variables in the 75$^{th}$ and higher percentiles were more likely to earn at least $10,000 per start.

Next, horses were first grouped by physical size, and then by heart measurement size. Table 36 shows that all groups of horses with HTWT percentiles of 75-100% (right-hand column) produced higher than average percentages of horses with earnings per start (EPS) ≧$10,000. All groups of horses with HTWT percentiles of 0-25% (left-hand column) produced fewer than average percentages of horses with EPS ≧ $10,000, regardless of heart measurement size.

Shaded areas in Table 36 show groups with higher than average percentages of horses with EPS ≧$10,000. Horses with HTWT percentiles in the 25-50% range generally performed as well as average as long as cardiac variables were above average.

The highest percentages of high earners occurred when percentiles for both HTWT and heart size were at least 75%. In cases where HTWT and heart size percentiles were at least 75%, the average percentage of horses with EPS ≧$10,000 was 23.0% (excluding PS)—a 73% improvement over random odds of selecting high earners (13.3% vs. 23.0%).

TABLE 36

Percentage of Horses that Earned at least $10,000 Per Start Based
on Percentiles for Individual Cardiac Variables Combined with HTWT

| | | HTWT | | | |
|---|---|---|---|---|---|
| | | 0-25% | 25-50% | 50-75% | 75-100% |
| 0-25% | LVD | 6.7 | 10.4 | 13.7 | 16.4 |
| | LVS | 6.9 | 10.5 | 12.3 | 16.2 |
| | SW | 6.7 | 12.3 | 11.3 | 13.5 |
| | PS | 7.8 | 13.1 | 15.1 | 21.4 |
| 25-50% | LVD | 9.4 | 9.6 | 11.9 | 13.4 |
| | LVS | 8.0 | 10.9 | 14.5 | 14.0 |
| | SW | 7.0 | 11.4 | 14.7 | 18.3 |
| | PS | 5.9 | 10.4 | 13.2 | 15.4 |
| 50-75% | LVD | 4.7 | 15.2 | 14.5 | 18.8 |
| | LVS | 7.3 | 14.6 | 15.9 | 16.9 |
| | SW | 9.1 | 12.3 | 14.4 | 16.4 |
| | PS | 8.3 | 13.4 | 14.6 | 19.2 |
| 75-100% | LVD | 11.0 | 16.8 | 17.9 | 22.2 |
| | LVS | 8.4 | 16.0 | 15.1 | 24.0 |
| | SW | 7.5 | 15.8 | 17.6 | 22.7 |
| | PS | 8.2 | 14.0 | 15.0 | 15.3 |

Above average performance categories are shaded.

Chi-square analysis was used to examine how Thoroughbreds' normalized heart size (as measured by LVD, LVS, PS, and SW) and normalized physical size (as measured by HTWT, which is the product of height times weight) relate to subsequent earnings and racing distances. Chi-square methods were used to show the predictive nature of each variable individually. Chi-square methods were then used to show the predictive nature of each cardiac variable, when used in conjunction with HTWT.

High earners and high earner routers were more likely to be above average in normalized physical size and normalized heart size (as measured by LVD, LVS, and SW). Low earners were more likely to be below average in normalized physical size and normalized heart size. High earner sprinters tended to be above average in normalized physical size with thick heart walls (as measured by normalized SW).

Statistics describing these relationships were summarized in tables 37-52.

Extremely high earners—Among 3,150 horses that raced at least three times by the end of their three-year-old year, 101 (3.2%) earned at least $250,000 and had earnings per start of at least $20,000. The following tables show the percentage of extremely high earners with various combinations of above and below average normalized HTWT and normalized cardiac measurements (LVD, LVS, SW and PS).

The following tables, Tables 37-40, show that a disproportionately high percentage of extremely high earners were large physically (for their sex, and chronological age), and had large hearts even relative to other large horses, i.e., when cardiac measurement variables were normalized for sex, chronological age, and physical size. Extremely high earners were three times more likely to have above average normalized HTWT and normalized cardiac measurements than to have below average normalized HTWT and normalized cardiac measurements. When breaking normalized HTWT categories down further, 4% of extremely high earners had HTWT of 0-25%, while 38% had HTWT of 75-100%—a nearly ten-fold difference. The general population, e.g., when not looking at racing performance success variables, is fairly evenly distributed among the four quartiles listed in the tables.

TABLE 37

| | | HTWT | |
|---|---|---|---|
| | | Below Average | Above Average |
| LVD | Below Average | 17% | 19% |
| | Above Average | 15% | 50% |

TABLE 38

| | | HTWT | |
|---|---|---|---|
| | | Below Average | Above Average |
| SW | Below Average | 15% | 23% |
| | Above Average | 17% | 46% |

TABLE 39

| | | HTWT | |
|---|---|---|---|
| | | Below Average | Above Average |
| LVS | Below Average | 18% | 24% |
| | Above Average | 14% | 45% |

TABLE 40

| | | HTWT | |
|---|---|---|---|
| | | Below Average | Above Average |
| PS | Below Average | 12% | 31% |
| | Above Average | 20% | 38% |

The following tables, Table 41-Table 44, show the percentage of high earner routers with various combinations of above and below average normalized HTWT and normalized cardiac measurements (LVD, LVS, SW and PS).

These tables show that a disproportionately high percentage of high earner routers were large physically (compared to other subjects of the same sex and chronological age), and had large hearts even relative to other large horses, i.e., when normalized for sex, chronological age, height and weight. High earner routers were four times more likely to have above average normalized HTWT and normalized cardiac measurements than to have below average normalized HTWT and normalized cardiac measurements. The general population is fairly evenly distributed among the four quartiles listed in the tables when not considering the racing performance variables.

TABLE 41

| | | HTWT | |
|---|---|---|---|
| | | Below Average | Above Average |
| LVD | Below Average | 12% | 25% |
| | Above Average | 15% | 48% |

TABLE 42

| | | HTWT | |
|---|---|---|---|
| | | Below Average | Above Average |
| SW | Below Average | 10% | 31% |
| | Above Average | 16% | 43% |

TABLE 43

| | | HTWT | |
|---|---|---|---|
| | | Below Average | Above Average |
| LVS | Below Average | 13% | 26% |
| | Above Average | 14% | 47% |

TABLE 44

| | | HTWT | |
|---|---|---|---|
| | | Below Average | Above Average |
| PS | Below Average | 12% | 37% |
| | Above Average | 14% | 37% |

The following tables, Tables 45-48, show the percentage of high earner sprinters with various combinations of above and below average normalized HTWT and normalized cardiac measurements (LVD, LVS, SW and PS).

These tables show that high earner sprinters were fairly evenly distributed by normalized physical size and the two normalized heart size variables of LVD and LVS, especially compared to distributions of the same variables for high earner routers. However, the tables show that high earner sprinters were about 50% more likely to have been big physically (normalized HTWT) with above average normalized SW and/or PS, than to be small physically, with small SW and/or PS. High earner sprinters were most likely to be relatively big horses with thick heart walls (normalized SW). The general population, i.e., all levels of racing performance, and not just sprinters or high earner sprinters, is fairly evenly distributed among the four quartiles listed in the tables.

TABLE 45

|  |  | HTWT | |
|---|---|---|---|
|  |  | Below Average | Above Average |
| LVD | Below Average | 22% | 27% |
|  | Above Average | 24% | 26% |

TABLE 46

|  |  | HTWT | |
|---|---|---|---|
|  |  | Below Average | Above Average |
| SW | Below Average | 22% | 22% |
|  | Above Average | 25% | 32% |

TABLE 47

|  |  | HTWT | |
|---|---|---|---|
|  |  | Below Average | Above Average |
| LVS | Below Average | 23% | 28% |
|  | Above Average | 24% | 26% |

TABLE 48

|  |  | HTWT | |
|---|---|---|---|
|  |  | Below Average | Above Average |
| PS | Below Average | 19% | 23% |
|  | Above Average | 28% | 31% |

The following tables, Table 49-52 show the percentage of low earners with various combinations of above and below average normalized HTWT and normalized cardiac measurements (LVD, LVS, SW and PS).

These tables show that a disproportionately high percentage of low earners were relatively small physically, and had small hearts even relative to other small horses. Low earners were about 1.5 times more likely to have below average normalized HTWT and normalized cardiac measurements than to have above average normalized HTWT and normalized cardiac measurements. The general population is fairly evenly distributed among the four quartiles listed in the tables when not considering subsets of different levels of racing performance.

TABLE 49

|  |  | HTWT | |
|---|---|---|---|
|  |  | Below Average | Above Average |
| LVD | Below Average | 31% | 23% |
|  | Above Average | 25% | 20% |

TABLE 50

|  |  | HTWT | |
|---|---|---|---|
|  |  | Below Average | Above Average |
| SW | Below Average | 31% | 23% |
|  | Above Average | 25% | 20% |

TABLE 51

|  |  | HTWT | |
|---|---|---|---|
|  |  | Below Average | Above Average |
| LVS | Below Average | 32% | 23% |
|  | Above Average | 24% | 20% |

TABLE 52

|  |  | HTWT | |
|---|---|---|---|
|  |  | Below Average | Above Average |
| PS | Below Average | 28% | 21% |
|  | Above Average | 29% | 22% |

Example 11

Predicting Racing Performance

Discriminant results showed that a horse's weight and height were important predictive indices of subsequent performance, in terms of earnings and successful distances raced. Additionally, interventricular septal wall structural thickness (SW) as defined in FIG. 3, or cross-sectional spleen area (SPLN), were the most important predictive variable when differentiating between high and low earners. In addition to physical size, the left ventricle in diastole and systole (LVD and LVS) were the most important predictive variables when differentiating between successful sprinters and routers.

Several of the variables studied were highly correlated (i.e., similar). Discriminant models typically had very similar results when one or two variables were replaced with other variables with which they were highly correlated (e.g. LVS and LVD, or WT and HTWT).

In most cases, combined-sex discriminant models correctly identified the same horses that were correctly identified by the same-sex models.

Blind tests showed that cardiac parameters predicted subsequent racing performance with far greater accuracy than possible selecting horses from these groups at random. Models successfully differentiated not only between stakes- and claiming-caliber horses, but also between stakes- and allowance-caliber horses.

On average, blind test discriminant models improved random odds of identifying high earners (or routers) by 35 percent (i.e., going from a 30% probability of correctly identifying high earners without models to a 40% probability with models).

Stepwise and discriminant analyses beyond those presented here sometimes produced exceptional results for one group in the comparison, but unexceptional results for the other group. For example, a high vs. low earners model may accurately predict high earners, while just meeting random expectations among low earners. Multiple models differentiated by level of earnings may be needed in such instances. Model limitations have to be assessed relative to potential applications. Z-tests were helpful in determining the statistical strength of discriminant results for each individual group represented in the models.

Example 12

Using Subjective Visual Cardiac Parameters to Predict Racing Performance

Subjective ratings (ranging from 1=poor to 5=excellent) to describe the images on the ultrasound machine—visual impressions of ecogenicity (e.g., clarity, sharpness of contrast, type and symmetry of shapes, smoothness of functioning of structures) of the 2D images were recorded. These ratings were recorded as: Ecogenicity (EC and VEC); general shape of the image at diastole and systole (CATE and SQ); clarity and sharpness of contrast of left ventricle during diastole and systole (DCL and SCL); smoothness of left ventricle during diastole and systole (DSM and SSM); blood backflow from left ventricle during diastole and systole (DBF and SBF); double-beat wave (XB); overall irregularity of the heart image (IRRG); how well the valve closes (NVC); and overall clearness of image in diastole (PVAR).

Stepwise analysis identified statistically significant variables that could differentiate between groups of horses categorized as high and low earners.

The variables considered in the analysis were LVD, LVS, SW, PS, HTWT, EC, CATE, DCL, DSM, DBF, XB, VEC, SQ, SCL, SSM, SBF, IRRG, NVC, and PVAR. Among these variables, LVD, LVS, SW, PS were standardized for sex, age and weight, and HTWT was standardized for sex and age.

For high vs. low earners, with the additional consideration of visual ratings as described above, stepwise analysis identified the following significant variables Combined Sexes. HTWT, PVAR, SBF
Colts. SBF, HTWT, DSM
Fillies. HTWT, PVAR, SQ, DSM In order to work with higher numbers of horses for discriminant analyses using the subjective visual variables (assessed each on a scale from 1 to 5), horses for which there were only two-year-old race records were added to the groups of raced horses used elsewhere to assess racing performance levels in this study. These were horses born in 1998. Thus, unlike everywhere else in this monograph, this analysis of raced horses had some horses with two- and three-year-old race records and others with just two-year-old race records.

The variables used in discriminant analysis were those identified as significant by stepwise analysis. Only combined sex models were analyzed due to limited number of horses.

Non-Blind A-Z. Table 53 shows that among 394 horses, non-blind discriminant models improved the odds of correctly classifying high earners from 33.25% without models to 43.93% with models. They improved the odds of correctly classifying low earners from 66.75% without models to 75.11% with models. All results were statistically significant (P-values $\leq 0.0083$).

TABLE 53

Discriminant Model Results Using Subjective 1-5 Variables - High vs. Low Earners Non-Blind Tests -- Combined Sexes - Names Starting with Letters A-Z

| Category | Pre-Model Probability | | Post-Model Probability | | P-Value |
|---|---|---|---|---|---|
| | Ratio | Pct. | Ratio | Pct. | |
| High Earners | 131/394 | 33.25 | 76/173 | 43.93 | 0.0029 |
| Low Earners | 263/394 | 66.75 | 166/221 | 75.11 | 0.0083 |

Non-Blind A-M. Table 54 shows that among horses with names beginning with the letters A-M, non-blind discriminant models improved the odds of correctly classifying high earners from 34.18% without models to 41.28% with models. They improved the odds of correctly classifying low earners from 65.82% without models to 71.88% with models. Results were not statistically significant (P $\leq 0.1499$).

TABLE 54

Discriminant Model Results Using Subjective 1-5 Variables - High vs. Low Earners Non-Blind Tests -- Combined Sexes - Names Starting with Letters A-M

| Category | Pre-Model Probability | | Post-Model Probability | | P-Value |
|---|---|---|---|---|---|
| | Ratio | Pct. | Ratio | Pct. | |
| High Earners | 81/237 | 34.18 | 45/109 | 41.28 | 0.1188 |
| Low Earners | 156/237 | 65.82 | 92/128 | 71.88 | 0.1499 |

Blind N-Z. Table 55 shows that among horses with names beginning with the letters N-Z, blind discriminant models based on the A-M horses improved the odds of correctly classifying high earners from 31.85% without models to 43.42% with models. They improved the odds of correctly classifying low earners from 68.15% without models to 79.01% with models. All results were statistically significant (P-values $\leq 0.0444$).

TABLE 55

Discriminant Model Results Using Subjective 1-5 Variables - High vs. Low Earners Blind Test -- Combined Sexes - Names Starting with Letters N-Z

| Category | Pre-Model Probability | | Post-Model Probability | | P-Value |
|---|---|---|---|---|---|
| | Ratio | Pct. | Ratio | Pct. | |
| High Earners | 50/157 | 31.85 | 33/76 | 43.42 | 0.0300 |
| Low Earners | 107/157 | 68.15 | 64/81 | 79.01 | 0.0444 |

What is claimed:

1. A non-transitory computer-readable storage medium for selecting a racehorse candidate having a better than average likelihood of becoming a high earner, the computer-readable storage medium having stored therein computer executable instructions that when executed by a processor cause the processor to perform the steps comprising:
   (i) receiving first data indicative of an ultrasonographically-obtained measurement of the width of the ventricular septal wall of an unraced racehorse candidate;
   (ii) retrieving a stored data set comprising ultrasonographically-obtained measurements from a group of horses, wherein said collection of measurements comprises ventricular septal wall width measurements for at least about 75 horses of about the same age, sex, and weight as said racehorse candidate; and
   (iii) generating a prediction indication from a comparison of the first data and the data set, wherein the comparison determines whether the unraced racehorse candidate has an ultrasonographically-obtained ventricular septal wall width measurement that is greater than the mean ultrasonographically-obtained ventricular septal wall width measurement from said data set, said determination based on a comparison of said first data with said data set; and
   (iv) outputting the prediction indication.

2. The non-transitory computer-readable medium of claim 1, wherein said comparison of the first data and the data set determines whether said unraced racehorse candidate has a ventricular septal wall width that is in the 75th percentile or higher as compared to the ventricular septal wall width measurements from said data set.

3. A computer system for selecting an unraced racehorse candidate having a better than average likelihood of becoming a high earner, the computer system comprising:
   a memory having stored therein a data set comprising ultrasonographically-obtained measurements from a group of horses, wherein said collection of measurements comprises ventricular septal wall width measurements for at least about 75 horses of about the same age, sex, and weight as said racehorse candidate; and
   a processor that (i) receives first data indicative of an ultrasonographically-obtained measurement of the width of the ventricular septal wall of said racehorse candidate, (ii) retrieves the data set from the memory, (iii) generates a prediction indication from a comparison of the first data and the data set, wherein the comparison determines whether the racehorse candidate has an ultrasonographically-obtained ventricular septal wall width measurement that is greater than the mean ultrasonographically-obtained ventricular septal wall width measurement from said data set, and (iv) outputs the prediction indication.

4. The computer system of claim 3, wherein said comparison of the first data and the data set determines whether said racehorse candidate has a ventricular septal wall width that is in the 75th percentile or higher as compared to the ventricular septal wall width measurements from said data set.

5. An racehorse candidate selection computer system for selecting a racehorse candidate having a better than average likelihood of becoming a high earner comprising:
   an ultrasound imaging machine with electronic calipers to generate first data indicative of a measurement of the width of the ventricular septal wall of an unraced racehorse candidate;
   a memory having stored therein a data set comprising ultrasonographically-obtained measurements from a group of horses, wherein said collection of measurements comprises ventricular septal wall width measurements for at least about 75 horses of about the same age, sex, and weight as said racehorse candidate; and
   a processor that (i) receives first data indicative of an ultrasonographically-obtained measurement of the width of the ventricular septal wall of said unraced racehorse candidate, (ii) retrieves the data set from the memory, (iii) generates a prediction indication from a comparison of the first data and the data set, wherein the comparison determines whether the unraced racehorse candidate has an ultrasonographically-obtained ventricular septal wall width measurement that is greater than the mean ultrasonographically-obtained ventricular septal wall width measurement from said data set, and (iv) outputs the prediction indication.

6. The system of claim 5, wherein said comparison of the first data and the data set determines whether said unraced racehorse candidate has a ventricular septal wall width that is in the 75th percentile or higher as compared to the ventricular septal wall width measurements from said data set.

* * * * *